United States Patent [19]
Becker

[11] Patent Number: 6,059,561
[45] Date of Patent: *May 9, 2000

[54] COMPOSITIONS AND METHODS FOR DETECTING AND QUANTIFYING BIOLOGICAL SAMPLES

[75] Inventor: Michael McClellan Becker, San Diego, Calif.

[73] Assignee: Gen-Probe Incorporated, San Diego, Calif.

[*] Notice: This patent is subject to a terminal disclaimer.

[21] Appl. No.: 09/094,139

[22] Filed: Jun. 9, 1998

Related U.S. Application Data

[63] Continuation of application No. 08/475,334, Jun. 7, 1995, Pat. No. 5,879,885.

[51] Int. Cl.$^7$ ............................ C12Q 1/68; G01N 33/566; C07H 19/00; C07H 21/00

[52] U.S. Cl. .............................. 431/6; 436/501; 436/518; 436/829; 536/22.1; 536/24.3; 536/25.32; 435/7.1

[58] Field of Search ..................... 435/6, 7.1; 436/501, 436/518, 829; 536/22.1, 24.3, 25.32

[56] References Cited

U.S. PATENT DOCUMENTS

| | | | |
|---|---|---|---|
| 3,654,090 | 4/1972 | Schuurs et al. | 195/103.5 |
| 4,174,384 | 11/1979 | Ullman et al. | 424/8 |
| 4,199,559 | 4/1980 | Ullman et al. | 424/8 |
| 4,318,707 | 3/1982 | Litman et al. | 23/8 |
| 4,383,031 | 5/1983 | Boguslaski et al. | 435/7 |
| 4,640,898 | 2/1987 | Halfman | 436/546 |
| 4,816,419 | 3/1989 | Halfman | 436/546 |
| 4,927,769 | 5/1990 | Chang et al. | 436/18 |
| 5,093,270 | 3/1992 | Chang et al. | 436/518 |
| 5,279,940 | 1/1994 | Kissel | 435/6 |
| 5,283,174 | 2/1994 | Arnold, Jr. et al. | 435/6 |
| 5,300,635 | 4/1994 | Macfarlane | 536/25.4 |
| 5,879,885 | 3/1999 | Becker | 435/6 |

FOREIGN PATENT DOCUMENTS

| | | |
|---|---|---|
| 0309230 | 3/1989 | European Pat. Off. |
| 0313219 | 4/1989 | European Pat. Off. |
| 0352713 | 1/1990 | European Pat. Off. |
| 0492570 | 7/1992 | European Pat. Off. |
| 0709466 | 5/1996 | European Pat. Off. |
| 8904375 | 5/1989 | WIPO |

OTHER PUBLICATIONS

Schmidt, "A rapid chemiluminescence detection method for PCR–amplified HIV–1 DNA", J. Virol. Meth., 32:233–244, (1991).

Kamidate, et al., "Enhanced luminescence of lucigenin with epinephrine in cationic surfactant micelles containing periodate", J. Biolumin. Chemilumin., 10:55–61, (Jan. 1995).

Memoli, et al., "Effects of surfactants on the spectral behaviour of calcein", J. Pharm. Biomed. Anal., 12(3):307–312, (Mar. 1994).

Papadopoulos, et al., "Chemiluminescence in organized molecular assemblies: Lucigenin derivatives containing long alkyl chains in micellar media", Anal. Chim. Acta, 290:179–185, (1994).

Nelson, et al., "Chemiluminescent DNA probes: a comparison of the acridinium ester and dioxetane detection systems and their use in clinical diagnostic assays", Clin. Chim. Acta, 194:73–90, (1990).

(List continued on next page.)

*Primary Examiner*—Jezia Riley
*Attorney, Agent, or Firm*—Charles B. Cappellari; Carlos A. Fisher

[57] ABSTRACT

Methods and compositions for selectively detecting analytes in a homogeneous assay, a heterogeneous assay, or a mixture of the two by contacting a labeled probe:analyte complex with one or more amphiphiles. The invention is also useful for increasing the signal to noise ratio when used in conjunction with other assay systems. In preferred embodiments, the analyte and probe are nucleic acids or proteins.

75 Claims, 24 Drawing Sheets

OTHER PUBLICATIONS

Ban, et al., "Fluorescence decay of the acridine orange–sodium dodecyl sulfate system: formation of dye rich induced micelles in the premicellar region", Photochem. Photobiol. 37(2):131–139, (Feb. 1983).

Gehlen, et al., "Fluorescence quenching of acridine orange by aromatic amines in cationic, anionic and non–ionic micelles", J. Photochem. Photobiol. A:Chem., 59:335–340, (1991).

Bagazgoitia et al., "Effect of Surfactants on the Intensity of Chemiluminescence Emission from Acridinium Ester Labelled Proteins," J. Biolum. Chemilum., 2:121–128 (1988).

Hinze et al., "Micelle–Enhanced Chemiluminescence and Application to the Determination of Biological Reductants Using Lucigenin," Anal. Chem., 56:2180–2191 (1984).

Howie et al., "Effect of Micelles and Cyclodextrin Solutions on Acridinium Chemiluminescence," in Bioluminescence and Chemiluminescence 415 (Scholmerich et al. eds. 1987).

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:1:

GCTCGTTGCG GGACTTAACC CAACAT      26

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:2:

ATGTTGGGTT AAGTCCCGCA ACGAGC      26

(2) INFORMATION FOR SEQ ID NO:3:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (xi) SEQUENCE DESCRIPTION: SEQ ID NO:3:

CTAAAGCGCT TTCCACCACA AGAC                                              24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

GTCTTGTGGT GGAAAGCGCT TTAG                                              24

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

CAGAACTCCA CACCCCCGAA G                                                 21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

CTTCGGGGGT GTGGAGTTCT G                                                 21

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:7:

GGGGTTCTTT TCGCCTTTCC CTCACGG                                           27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:8:

CCGTGAGGGA AAGGCGAAAA GAACCCC                                           27

(2) INFORMATION FOR SEQ ID NO:9:

-continued

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

CCAGATGTGT TCAACTAGGA GTCCTGATCC                                                30

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:10:

CCAGACATAG TTATCTATCA ATACATGGAT GAT                                            33

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:11:

ATCATCCATG TATTGACAGA TAACTATGTC TGG                                            33

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:12:

ATCATCCATG TATTGATAGA TAACTATGTC TGG                                            33

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

CCAGACATAG TTATCTGTCA ATACATGGAT GAT                                            33
```

COMPOSITIONS AND METHODS FOR DETECTING AND QUANTIFYING BIOLOGICAL SAMPLES

This application is a continuation of application Ser. No. 08/475,334, filed on Jun. 7, 1995, now U.S. Pat. No. 5,879,885.

FIELD OF THE INVENTION

This invention concerns compositions and methods for detecting and quantifying biological analytes. More particularly, the invention relates to the detection of biological analytes using methods employing the applied disciplines of molecular biology and/or immunology. Applications of such detection methods and compositions include the diagnosis of human or animal disease and infection, the testing of foods and other products intended for human consumption, and forensic and environmental testing.

BACKGROUND OF THE INVENTION

The detection and quantification of microorganisms and viruses and biological molecules such as nucleic acids and proteins has important implications in many fields, including the diagnosis of human disease and infection and in food and environmental testing. Additionally, the detection or quantification of specific biomolecules from tissue, sputum, urine, blood, semen, saliva and other biological materials plays an increasingly important role in various fields including, without limitation, the identification of criminal suspects and in paternity testing.

Currently such testing procedures and assays commonly utilize nucleic acids or proteins as molecular probes with which to identify the presence of specific organisms, tissues, or molecules in a given sample. For example, nucleic acid probes and-proteins such as antibodies can be "labeled", or linked to a detectable moiety such as a radionuclide, an enzyme (or enzyme substrate) capable of participating in a predetermined chemical reaction which can be independently monitored, or a fluorescent, luminescent or chemiluminescent compound. When the labeled probe molecule is exposed to a specific analyte under conditions allowing the probe and analyte to associate, the amount of associated label is correlated to the amount of analyte originally present in the sample.

While both nucleic acids and antibodies can be used as molecular probe, one of these types of probe may be more suitable than the other in a given application. For example, single-stranded nucleic acids are most often used in methods to detect target nucleic acids in a sample having nucleotide sequences complementary to that of the probe.

By a nucleotide sequence is meant an order of consecutive nucleotides (e.g., the phosphate esters of adenosine (A), thymidine (T), cytosine (C), guanadine (G), inosine (I) and uracil (U)) comprising a single-stranded nucleic acid, conventionally described from the 5' terminus to the 3' terminus of the subject nucleic acid strand. Under appropriate reaction conditions a single-stranded nucleic acid may hybridize with another single-stranded nucleic acid to form a double-stranded helical structure held together by hydrogen bonds between pairs of complementary bases on opposing strands. Generally in such a structure, A is hydrogen bonded to T or U, while G or I are hydrogen bonded to C (although occasional mismatches may occur without causing strand separation); in such a case each nucleic acid strand is said to be complementary to the other nucleic acid strand. Thus, nucleic acid probes are most commonly used to detect other nucleic acids in a target region of nucleotide sequence complementarity.

Because of the sequence-specific nature of nucleic acid hybridization, and because of evolutionary divergence of species at the nucleotide sequence level, nucleic acid probes are often more suitable for detecting a given species of organism than are antibody probes. Nucleic acid probes can be exquisitely sensitive. For example, small amounts of target nucleic acids can be amplified using methods such as the polymerase chain reaction (e.g., EPO 0 200 362) and transcription-based amplification systems (e.g., WO 91/01384, WO 93/22461 and WO 94/03472), and can then be detected using specific oligonucleotide probes. Nucleic acid probes can also effectively distinguish slight differences (sometimes a single mismatch) between versions of the same gene or nucleotide sequence, which can permit diagnostic screening for genetic defects or mutations. Nucleic acid probes can be used in the identification of a particular individual within a species, for example to discount or even identify a criminal suspect by screening specimens of his or her nucleic acids.

Antibodies also remain effective tools for the identification and detection of specific cells, viruses, and proteins. Immunodiagnostic methods can thus be used to test for the presence of a specific disease or infection state, genetic defect, or physiological condition connected with the specific antigen or substance sought to be detected.

The majority of assay methods employing nucleic acids and/or antibodies utilize a physical binding step in order to separate the probe:analyte complex from unbound probe. These assay methods are called "heterogeneous" assays. By "probe:analyte complex" or "probe:analyte conjugate" is meant a specifically-associated molecular species containing at least one antibody or nucleic acid probe molecule (preferably labeled with a detectable moiety or atom) in stable association with at least one analyte molecule. An analyte molecule is a molecular species such as a nucleic acid or antigen sought to be detected, quantitated and/or identified.

A "hybrid"or "probe:analyte hybrid" is a probe:analyte complex in which probe and analyte are both nucleic acids.

Assay methods utilizing a physical separation step may employ a solid phase matrix, such as glass, minerals or polymeric materials in the separation process. The separation may involve preferentially binding the probe:analyte complex to the solid phase matrix while allowing the unassociated probe molecules to remain in a liquid phase. In such a case the amount of probe bound to the solid phase support after a washing step is proportional to the amount of analyte in the sample. Alternatively, the assay may involve preferentially binding the unassociated probe while leaving the probe:analyte complex to remain in the liquid phase; in this case the amount of probe in the liquid phase, again after a washing step, is proportional to the amount of analyte in the original sample. When the probe is a nucleic acid or oligonucleotide the solid support can include, without limitation, an adsorbent such as hydroxylapatite, a polycationic moiety, a hydrophobic or "reverse phase" material, an ion-exchange matrix such as DEAE, a gel filtration matrix, or a combination of one or more of these solid phase materials. In the case of media such as gel filtration, the separation is not due to binding of the oligonucleotide but is caused by molecular sieving of differently sized or shaped molecules.

A heterogeneous assay method may also involve binding the probe to a solid phase matrix prior to addition of a sample suspected of containing the analyte of interest. The sample can be contacted with the label under conditions which would cause the analyte of interest to be labeled, if present in the sample mixture. The solid phase matrix may be derivatized or activated so that a covalent bond is formed between the probe and the matrix; alternatively, the probe may be bound to the matrix through strong non-covalent interactions, including, without limitation: ionic, hydrophobic, reverse-phase, immunobinding, chelating, and enzyme-substrate interactions. After the matrix-bound probe is exposed to the labeled analyte under conditions allowing the formation of a probe:analyte complex, the separation step is accomplished by washing the solid phase matrix free of any unbound labeled analyte. Conversely, the analyte can be bound to the solid phase matrix and contacted with labeled probe, with the excess free probe washed from the matrix before detection.

Yet another type of assay system is termed a "homogeneous assay"; such assays can generally take place in solution without a solid phase separation step and commonly exploit chemical differences between the free probe and the analyte:probe complex. An example of an assay system which can be used in a homogenous format is the hybridization protection assay (HPA) disclosed in U.S. Pat. No. 5,283,174, in which a probe is linked to a chemiluminescent moiety, contacted with a analyte and then subjected to selective chemical degradation or detectable change in stability under conditions which alter the chemiluminescent reagent bound to unhybridized probe without altering the chemiluminescent reagent bound to an analyte:probe conjugate. This patent enjoys common ownership with the present application and is incorporated by reference herein.

Competition assays in which a labeled probe or analyte competes for binding with its unlabeled analog, are also commonly used in a heterogeneous format. Depending on how such a system is designed, either the amount of bound, labeled probe or the amount of unbound, labeled probe can be correlated with the amount of analyte in a sample. However, such an assay can also be used in a homogeneous format without a physical separation step, or in a format incorporating elements of both a homogeneous and a heterogeneous assay.

The present invention may be used in a homogeneous format, a heterogeneous format, or a mixture of formats as outlined above. It relates to assays in which there is caused a reversible difference in the detectability of a label when coupled to a substance forming a complex or conjugate with the analyte, as opposed to when it is not so coupled. In a preferred aspect, the invention is concerned with means for establishing an environment in which a labeled substance is differentially detected in a complexed or bound form, as opposed to a "free" or unbound form.

A particular object of the present invention is to provide a method for detecting, identifying or measuring an analyte in which the detection method is based on the relationship of the label to its microenvironment, thus allowing the label to differentiate between a "bound" state and an "unbound" state, relative to the substance to which it is coupled. Another object of the present invention is to provide methods for altering the microenvironment of the labeled substance so as to exploit the ability of the label to so differentiate.

A further object of the invention is to provide an assay method which is simple and minimizes the number of operator steps necessary to obtain a result. Thus, the present invention is especially useful in a homogenous format wherein detection of the binding pair is accomplished without a physical separation step, although as mentioned above, the methods and compositions described herein may easily be adapted to include such a step if desired.

Still further, it is an object of the invention to provide a method of decreasing the amount of background signal in a diagnostic assay, thereby increasing the signal-to-noise ratio for the assay which may in turn allow the detection of smaller quantities of analyte in the original sample. Such an improvement in the sensitivity of diagnostic assays supplies a clear advantage in the prompt and accurate identification of, for example, trace amounts of pathogenetic bacteria, fungi, or virions in a patient specimen, which in turn can allow for more rapid and accurate diagnosis and treatment.

The following examples demonstrate the methods and compositions of the present invention utilizing light-emitting substances, specifically chemiluminescent and luminescent compounds, as labels. It will nevertheless be clear to those of ordinary skill in light of the present disclosure that the present invention is equally applicable to assay formats utilizing other types of detectable compounds as labeling agents, such as a fluorescent agent so long as the compound is susceptible to sequestration between a probe:analyte complex and a detergent micelle and one of these microenvironments quenches or inhibits the detectability of the label. In the present invention such sequestration occurs depending upon whether the probe to which the labeling compound is coupled is complexed with the analyte of interest or exists in an unbound or "free" state in the assay medium.

By "quench" is meant to prevent a labeling substance from being detected or detectable, and may act either directly or indirectly. In a preferred embodiment, quenching is accomplished through the use of a substance which prevents a triggering agent from reacting with a label (such as a chemiluminescent label), resulting in the inability of the quenched label to be made detectable as, for example, by the emmission of light. Alternatively, the quenching agent may interact with the label thereby absorbing energy emitted by the label, as is the case when, for example, the fluorescent label 1,5-IEDANS (Molecular Probes, Eugene, Oreg.) interacts with the quencher moiety DABCYL (Molecular Probes, Eugene, Oreg.) to prevent the emission of fluorescent light.

An assay format known as HPA (the hybridization protection assay), in which assay selectivity is based on the molecular microenvironment of the labeling reagent, is described (as mentioned above) in U.S. Pat. No. 5,283,174. In the HPA format an analyte-binding probe is joined to a labeling substance which undergoes differential degradation unless the labeled probe forms a stable complex with the analyte of interest. Addition of an oxidizing agent as hydrogen peroxide results in detectable chemiluminescence only from intact analyte associated label.

Another type of assay format in which the activity of the label is different depending on whether the substance to which it is coupled is bound to the analyte or not typically uses an enzyme as a label. The probe-coupled enzyme uses a substrate to elicit a colorimetric, fluorometric or chemiluminescent signal, which is then detected. Such formats are described in U.S. Pat. Nos. 3,654,090, 3,817,837, and 4,190,496.

In U.S. Pat. No. 5,093,270 there is described a method which uses liposome vesicles to encapsulate marker molecules, including fluorescent and chemiluminescent molecules, which are subsequently released from the liposomes using water-miscible alcohols. U.S. Pat. Nos. 4,640, 898 and 4,816,419 describe a competition assay for gentamicin utilizing charged SDS micelles to bind the oppositely charged gentamicin moiety of free fluorescein-labeled gentamycin; under the conditions described no such binding occurred when the gentamicin was conjugated with a specific antibody. The fluorescein label's intensity and changes in the polarity of emitted light were then detected.

Enhancement of fluorescent yield and changes of the polarization of the emitted light by surfactant micelles has been disclosed by Gratzel and Thomas, *The Application of Fluorescent Techniques to the Study of Micellar Systems* in 2 *Modern Fluorescent Spectroscopy* 169 (ed. E. L. Wehry 1976).

SUMMARY OF THE INVENTION

The present invention relates to qualitative and quantitative assay methods and compositions wherein a labeled probe's detectability is dependent upon whether the probe is bound to the analyte of interest or is "free" or unbound. The method involves the use of amphiphilic molecules, such as detergents (surfactants) or lipids to form micelles or liposomes. It is thought that the label molecules are sequestered within the micelles or liposomes when the probe is unbound, thus functioning to the extinguishing or diminishing the label's detectability. Under the same conditions, however, the label associated with a probe:analyte complex is not sequestered, and is thus available to be detected.

The present invention provides a simple, sensitive and inexpensive method for causing a labeling compound coupled to a molecular probe to become differentially detectable depending on whether the probe is stably complexed to its target analyte. By "probe" is meant any molecular species which will preferentially bind to or become stably associated with an analyte of interest. Thus, a probe includes, without limitation, a nucleic acid, a protein, an enzyme, an antibody, an antigen, a hapten, a carbohydrate, a lipid, a lipoprotein, a lipopolysaccharide, a nucleoprotein, a cellular receptor, a cell-binding protein, a dye or an intercalating agent. Likewise, an analyte may be, without limitation, an atom, a molecular species, complex or aggregate, a virion, a cell, a nucleic acid, a protein, an enzyme, an antibody, an antigen, a hapten, a carbohydrate, a lipid, a lipoprotein, a lipopolysaccharide, a nucleoprotein, a cellular receptor or a cell-binding protein.

In one embodiment the present invention is directed to a method for determining the presence or amount of an analyte which involves providing a) a probe capable of specifically binding to the analyte, b) a detectable label linked to the probe, where the detectability of the label is dependant upon whether the probe forms part of a probe:analyte conjugate or remains unbound, and c) a sample suspected of containing the analyte of interest. These elements are brought together under conditions which allow the probe and analyte to form a probe:analyte complex; an amount of an amphiphile, such as a surfactant or lipid sufficient to cause the formation of micelles (or lipid bilayers) is contacted with the binding pair and any unbound labeled probe. The label is then detected as a measure of the presence or amount of the analyte.

In a preferred embodiment, the label is a hydrophobic compound, for example a hydrophobic dye or fluorescent or chemiluminescent compound, which is also able to associate or intercalate with a double-stranded nucleic acid. In a particularly preferred embodiment, the detected compound is an N-substituted-9-acridone formed by oxidation of a precursor label compound, e.g., an acridinium ester derivative, with an oxidizing agent such as hydrogen peroxide, a peroxide-forming compound, or superoxide radical. The excited acridone emits electromagnetic radiation in the form of light, which is detectable and quantifiable using a luminometer.

In other embodiments the label is a chemiluminescent rhodamine derivative which is detectable when the probe is bound to the analyte, but which interacts with the micelles when the labeled probe remains unbound, to cause a quenching of the label's chemiluminescent potential.

In other preferred embodiments the probe and analyte are single-stranded nucleic acids which hybridize with each other to form a double-stranded nucleic acid hybrid complex.

In an embodiment, lipid bilayers are formed from at least one positively charged lipid wherein the interior of the bilayers are hydrophobic and the exterior of the bilayers are hydrophilic. In further embodiments, the hydrophobicity of the bilayer interior is altered by the addition of at least one other neutral or charged lipid or detergent.

In another preferred embodiment the surfactant micelles contain at least one charged surfactant species, preferably a cationic detergent having a hydrophobic "tail" and a positively charged "head" under the assay conditions. These terms are well-known to those familiar with detergent and lipid chemistry.

In another preferred embodiment, the surfactant micelles contain at least two detergent molecules having "tail" regions of different hydrophobicities. In this embodiment, mixing the surfactant molecules in different ratios allows the formation of a range of micelles with hydrophobic regions having hydrophobicities between that of the most hydrophobic and the least hydrophobic "tail" regions of the surfactants comprising them.

In a particularly preferred embodiment of the invention the micelles contain a mixture of at least one cationic surfactant species, particularly those selected from the group consisting of cetyl trimethyl ammonium salts, cetylpyridinium salts, cetyl dimethylethyl ammonium salts, 3-(cyclohexylamino)-2-hydroxyl-1propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts and benzalkonium salts, and may contain at least one other surfactant species, particularly those selected from the group consisting of surfactants of the TRITON® series, the Tween series, the Brij series and the NP series, most particularly selected from the group consisting of TRITON® X-100, TRITON® X-305, Tween 20, Brij 35 and NP-40.

The label may be coupled to the probe by any stable means, for example by hapten binding, through a chelating group, by antibody-antigen interactions or by covalent linkages. A linker moiety, for example an N-hydroxysuccinate group, may be used to couple the label to the probe. However, linkages having other groups able to join label and probe are known in the art. When the probe and analyte are both nucleic acids the Applicant currently prefers to use non-nucleotide linking reagents to couple the label to the probe, as disclosed in Arnold, et al., EPO 0 313 219, which enjoys common ownership with the present application and is hereby incorporated by reference herein.

Thus, it is an object of the present invention to provide methods and compositions useful for specifically detecting an analyte in solution without the need for a physical separation step to separate the analyte:probe binding pairs from the unbound labeled probe. However, the method of the present invention may be combined with a physical separation step if desired, for example to decrease any residual background of unbound labeled probe thereby increasing the signal-to-noise ratio of the assay system.

Moreover, it is another object of the invention to provide a method which may be combined with other assay methods, such as HPA, to increase the signal to noise ratio of the assay and the reproducability of the assay. It will also be understood that this method makes use of comparatively inexpensive reagents and compositions, and assay kits utilizing the compositions and methods described herein are much easier to assemble, package, and transport than other methods necessitating specialized equipment. Additionally, the invention provides assay methods which can quickly be performed in a single test vessel with a minimum of steps.

BRIEF DESCRIPTION OF THE DRAWINGS

FIG. 19, heading "B" is a plot of the chemiluminescence of probe-linked and hybrid-linked rhodamine, in the presence of a fixed concentration of CPC, as a function of increasing concentrations of TRITON X-100.

DETAILED DESCRIPTION OF THE INVENTION

Figure 1A:
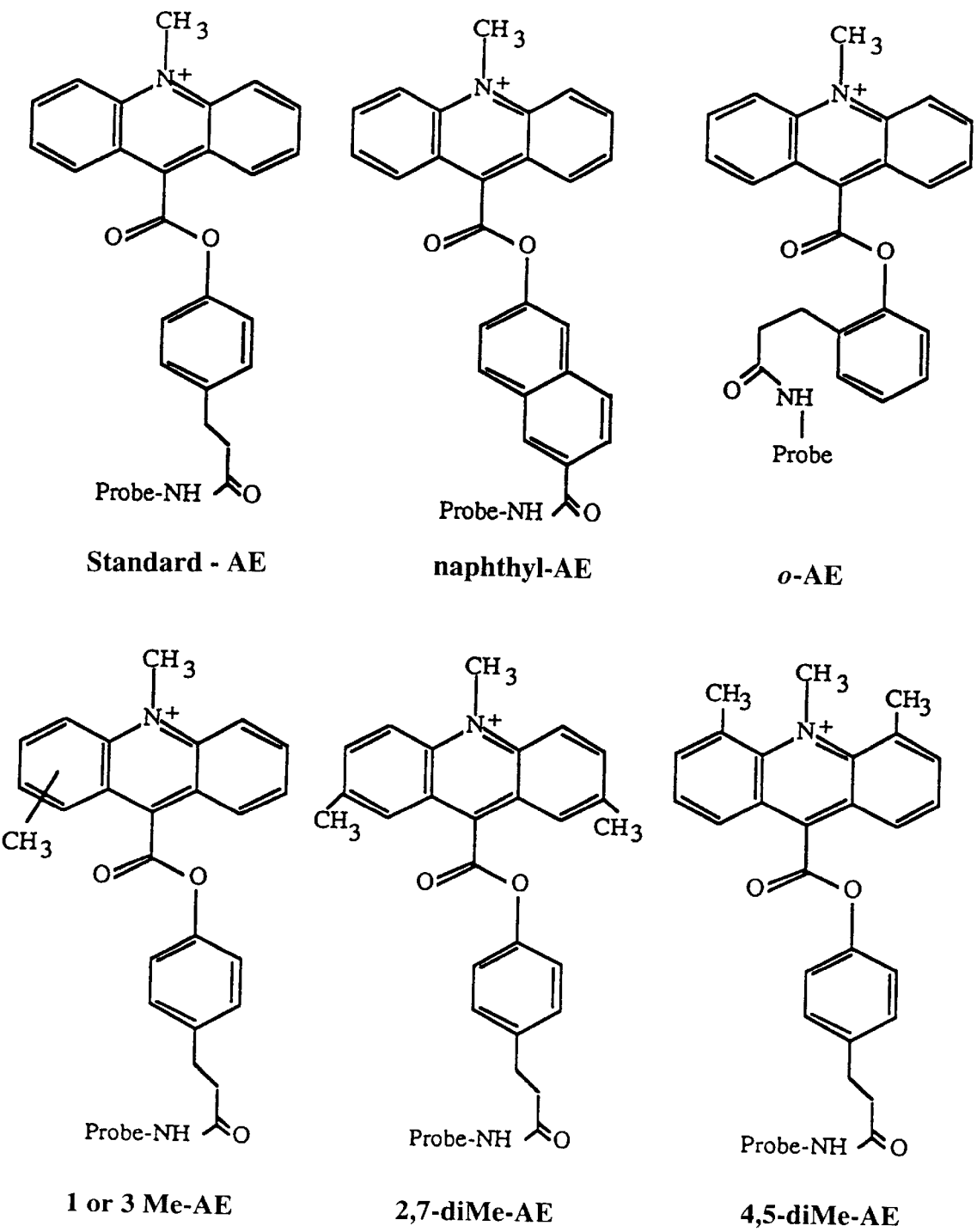
FIGS. 1A, 1B and 1C depicts the structures of various acridinium ester derivatives.
Figure 1B:
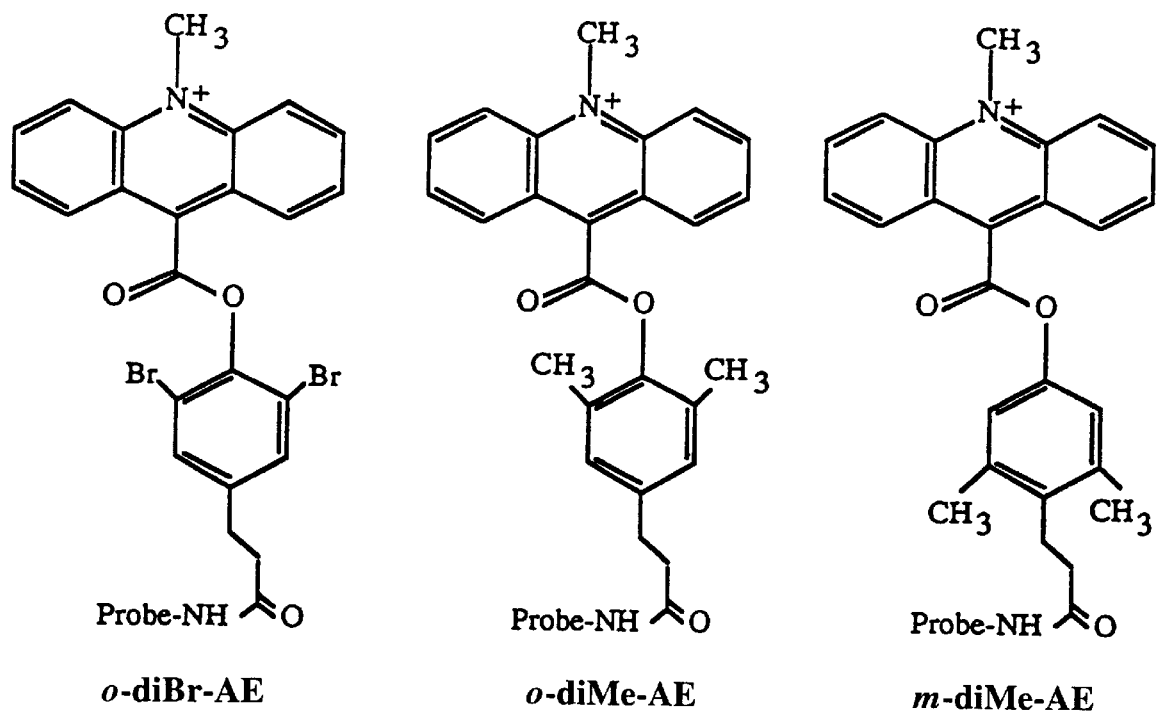
Figure 1B:
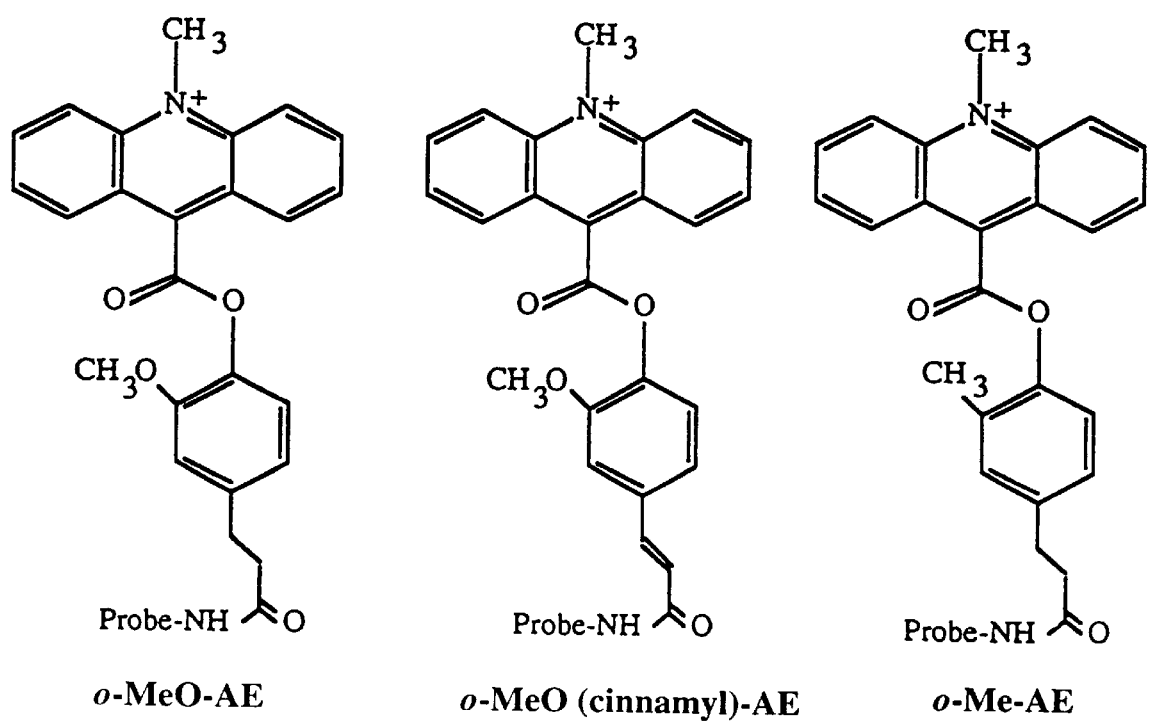
Figure 1C:
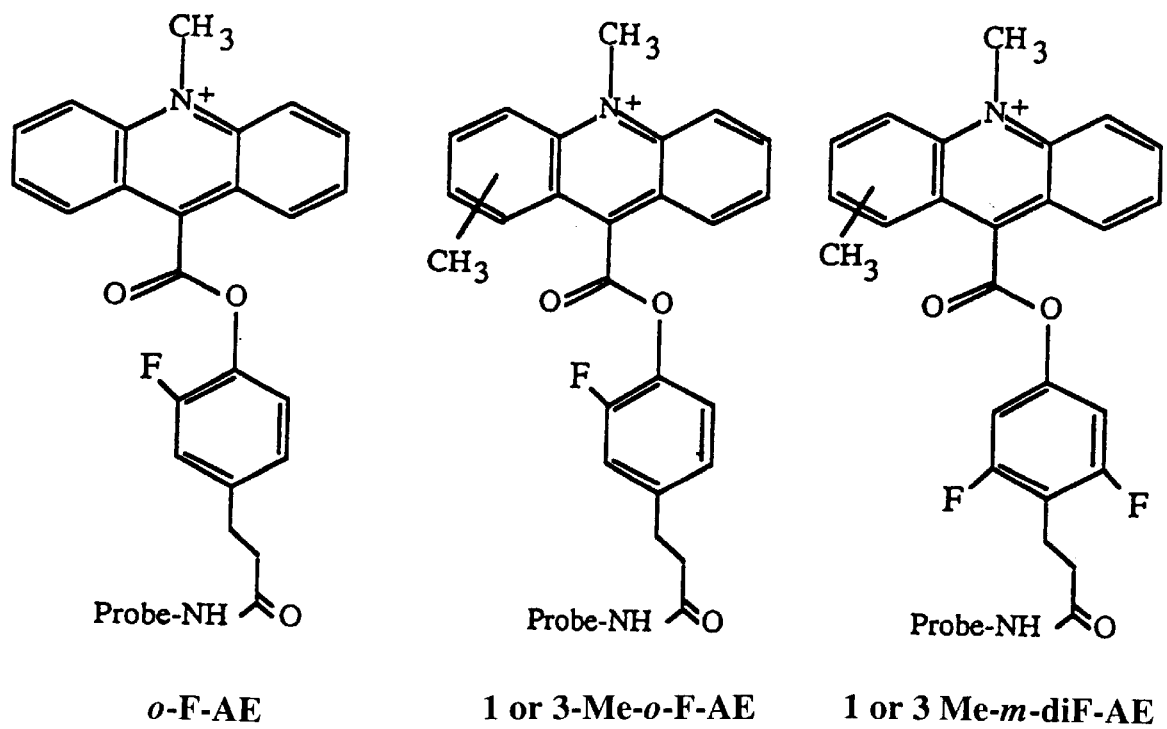
Figure 2A:
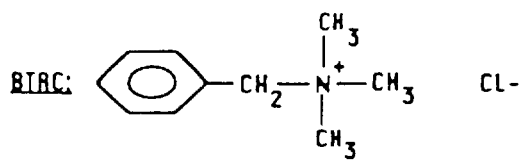
FIGS. 2A and 2B depicts the structures of various amphiphiles.
Figure 2A:
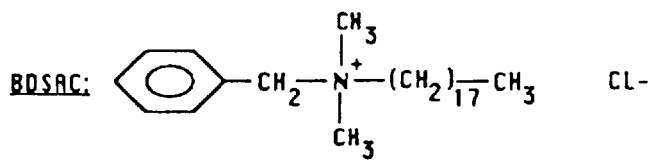
Figure 2A:
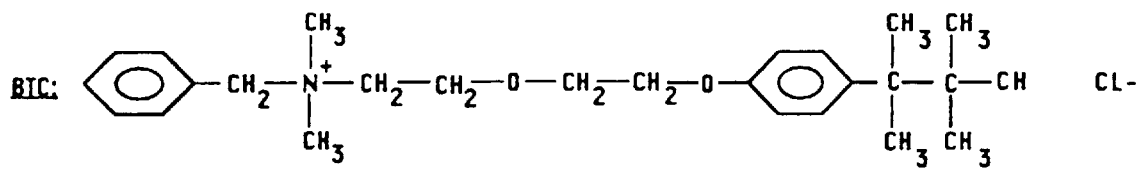
Figure 2A:
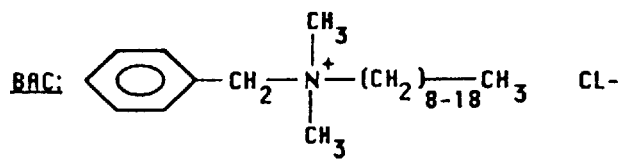
Figure 2A:
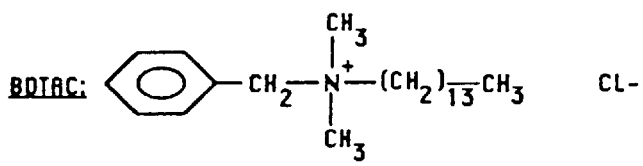
Figure 2A:
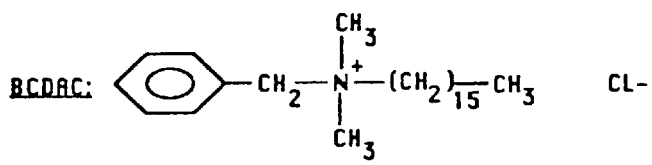
Figure 2A:
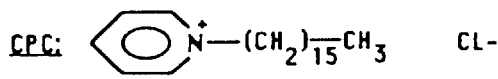
Figure 2A:
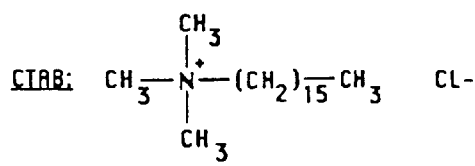
Figure 2A:
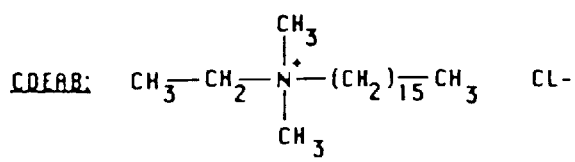
Figure 2B:
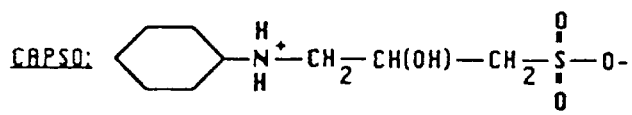
Figure 2B:
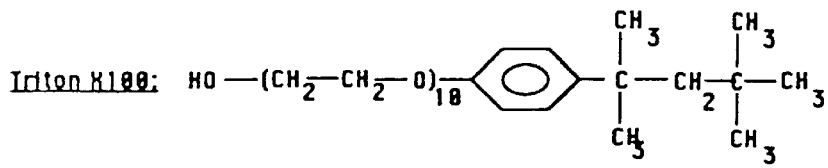
Figure 2B:
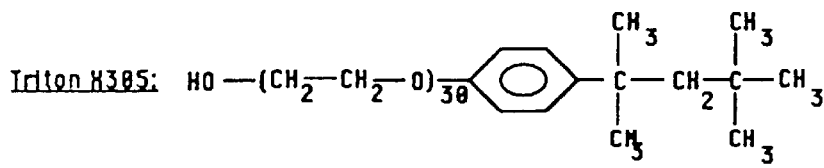
Figure 2B:
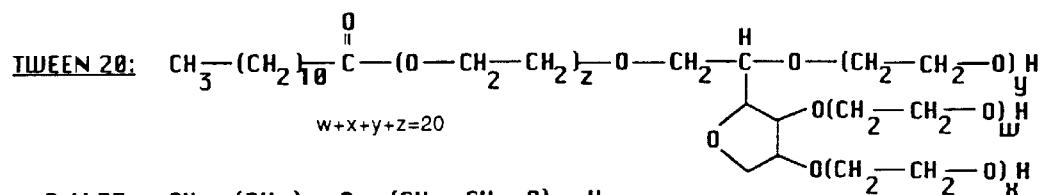
Figure 2B:
Figure 2B:
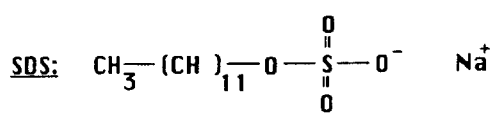
Figure 2B:
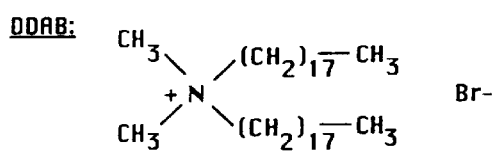
Figure 2B:
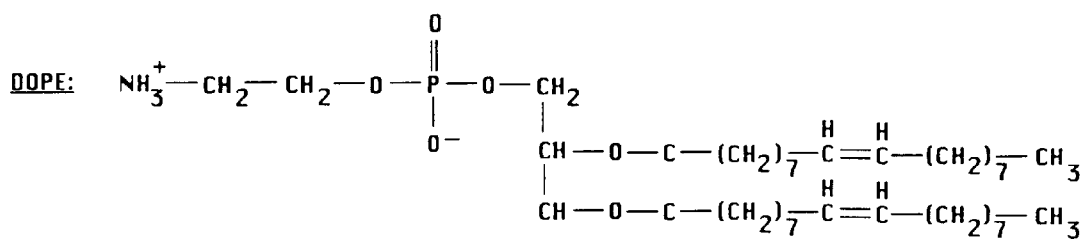

The present invention relates to qualitative and quantitative assay methods and compositions wherein a labeled probe's detectability is dependent upon whether the probe is bound to the analyte of interest or is "free" or unbound. The method involves the use of amphiphilic molecules, such as detergents (surfactants) or lipids to form micelles, liposomes or lipid bilayers. It is thought that under these conditions, the label molecules are sequestered within the hydrophobic interior of the micelles or bilayers when the probe is unbound, thus extinguishing or diminishing the probe-associated label's detectability, as explained below. The terms "surfactant" and "detergent" shall be used interchangeably herein to mean any of the class of amphiphilic molecules having separate hydrophobic and hydrophilic domains, and able to form homogeneous and/or heterogeneous micelles in solution. The term "lipid" shall be used to refer to amphiphilic molecules having separate hydrophobic and hydrophilic domains, and able to form homogeneous and/or heterogeneous liposomes or bilayers in solution; these lipids tend not to be as soluble in aqueous solution as are the detergents, and form liposomes or lipid bilayers rather than micelles. Nevertheless, the lipid bilayers consist of a hydrophobic interior and hydrophilic exterior surfaces; thus these structures are thought to function in a manner analogous to micelles in the present invention. Micelles are usually monolayered structures having a hydrophobic interior and a hydrophilic exterior. The term "amphiphile" shall refer to the group of chemical compounds, including surfactants and lipids, which have discrete hydrophilic and hydrophobic domains and which are able to form micelles, liposomes, bilayers or combinations of these structures.

While not wishing to be bound by theory, Applicant believes that the interior of the micelles or bilayers provides a hydrophobic environment to which labels having a hydrophobic moiety are attracted and held. When the labeled probe is in an unbound state, a hydrophobic portion of the label is sequestered by the hydrophobic interior of the micelle or lipid bilayer, which quenches the label's detectable signal. Alternatively, in the case of labels, such as chemiluminescent labels, which need to be activated or reacted (triggered) prior to becoming detectable, the micelle (or bilayer) is thought to provide a shield from exposure of the label to catalysts, reactants or cofactors necessary for the label's detectability. Such reagents are herein termed triggering agents, and the reaction in which they and the label participate to form a detactable signal is termed a triggering reaction.

By contrast, Applicant believes that the label coupled to probe molecules which are stably complexed with the analyte of interest does not become associated with the interior of the micelle or liposome, presumably due to stronger competing interactions of the label with the probe:analyte complex, and is therefore not quenched. Such probe:analyte complex-associated interactions are thought to be largely hydrophobic in nature.

In a particularly preferred embodiment of the present invention, the probe and analyte are both single-stranded nucleic acids, and the label is an N-acridinium phenyl ester derivative;

the acridinium ring may be substituted at one or more positions and the phenyl ring may also be substituted at one or more position so long as oxidation of the ester linkage results in the production of a light-emitting excited N-acridone. A non-exclusive list of acridinium ester (AE) derivatives is given in FIG. 1. In the simplest example of such an acridinium ester is 4-(2-succinimidyloxycarbonyl ethyl)-phenyl-10-methylacridinium-9-carboxylate fluorosulfonate (hereafter referred to as standard AE)$^-$, which is preferably linked via a non-nucleotide linker to or between the bases of an oligonucleotide probe. See EPO 0 313 219, supra, previously incorporated by reference. When the probe and analyte nucleic acids form a stable double-stranded hybrid there is created a major groove and a minor groove as part of the topology of the double helix.

However, chemiluminescent acridinium derivatives having groups other than phenyl, or having additional substituents are known in the art; see, e.g., Corning; McCapra, Hoescht; such derivatives would be expected by the skilled artisan to function in the present assay by virtue of their chemical similarity to the acridinium phenyl esters described herein.

In an embodiment of the present invention, an amount of a surfactant, e.g., the cationic detergent cetyl trimethyl ammonium bromide (CTAB), is added to the assay solution at a concentration sufficient to form micelles. Under these conditions the chemiluminescent potential of the acridinium ester label is strongly quenched, even when the label is coupled to the probe.

By "chemiluminescent potential" is meant the ability of a compound to emit light upon addition to the reaction mixture of a triggering agent such as a reactant or catalyst. In the case of acridinium ester derivatives, the triggering agent is any oxidizing agent (such as, without limitation, hydrogen peroxide, a hydrogen peroxide-producing compound, or a superoxide producing compound able to cause the production of a light-producing excited N-acridone.

By contrast, the addition of a surfactant to solutions containing labeled, hybridized probe can, at low concentrations of surfactant, result in an initial quenching of the chemiluminescent signal, followed by a gradual restoration of the chemiluminescent potential of hybrid-bound label with increasing detergent or lipid concentration.

In one embodiment of the present invention, an amount of TRITON® X-100 (polyoxyethylene alcohol) is added to a cationic surfactant such as CPC (cetyl pyridinium chloride) prior to micelle formation. In this system, the chemiluminescence emitted by the acridinium ester label coupled to hybridized probe is initially quenched but then increases to easily detectable levels with the addition of greater concentrations of TRITON® X-100. The label coupled to unhybridized probe, however, remains quenched after addition of the oxidizing agent, even with increasing amounts of the non-ionic detergent.

Although not wishing to be limited by theory, in the case of nucleic acid probes and analytes, the Applicant believes the acridinium ester derivatives linked to hybridized probe reside within the hydrophobic "pocket" formed in one or both of the grooves of the double helix. While the label which so resides remains susceptible to oxidation by hydrogen peroxide or superoxide radical (resulting in detectable light emission) the label is associated with the double groove strongly enough that the detergent micelles or lipid bilayers present a higher energy, less desirable environment for the hybrid-associated label. In the absence of the double-stranded environment the label coupled to unhybridized probe lacks this favored microenvironment and preferentially becomes associated with the hydrophobic interior of the micelles or bilayers.

In this or other embodiments another possibile mechanism is that a detectable label may preferentially intercalate between bases in the double helix more readily than become associated with the detergent micelles or lipid bilayers. Again, if the label has no helical structure to intercalate with it is more likely to be quenched by the hydrophobic interiors of the micelles or bilayers.

The sequestration phenomenon may be manipulated by varying the hydrophobicity of the micelle (or bilayer) interior relative to a specific probe:analyte conjugate. Depending on the nature of the label, the hydrophobicity of the micelle or bilayer interior can be "tuned", as by the mixture of amphiphiles having different types of hydrophobic "tail". Thus, an amphiphile having long unsubstituted aliphatic chains (such as CPC with its —$(CH_2)_{15}$—$CH_3$ tail) would be considered to have a "tail" more hydrophobic than that of an amphiphile having uncharged heteroatoms such as oxygen or sulfur (for example TRITON® X-100, which has a —(O—$CH_2$—$CH_2)_{18}$—OH tail). While all such hydrophobic tails are non-polar, the latter type have tails with greater dipole moments than the alkane tails of the former type, and are thus less hydrophobic. Thus, for example, the interior of micelles containing, for example, mixtures of these two surfactant types should therefore be of intermediate hydrophobicity relative to the two surfactant types comprising them. By adjusting the ratios of the detergents, one of ordinary skill in the art can, with the guidance of this disclosure, precisely control the hydrophobicity of the micelle interior.

This can allow the designing of micelles and bilayers which have interiors less hydrophobic than the probe:analyte conjugate but still hydrophobic enough to sequester the label associated with free probe. This will lead to optimization of the assay.

The present invention also contemplates that micelles may be made with amphiphiles having a charge opposite from that of either or both the probe or analyte molecules. For example, when probe and target are both negatively-charged nucleic acids, the micelles or bilayers may be made with cationic amphiphiles or mixtures of cationic and neutral amphiphiles which are able to concentrate the nucleic acids at the micelle surface. In such a case, the quenching of the label would be expected to be more efficient than in a system utilizing neutral amphiphiles only.

By an effective amount is meant an amount of amphiphile which will increase the signal-to-noise ratio between the labeled probe:analyte complex and free probe in an assay. In preferred embodiments the ratio of signal from the probe:analyte complex versus free probe-associated label "noise" is two-fold or greater, four-fold or greater, ten-fold or greater, twenty-fold or greater, fifty-fold or greater, one hundred-fold or greater and two hundred-fold or greater.

It will be understood that assay systems can vary greatly in their reproducability and precision, depending on factors including the type of instrument used to detect the label the nature of the label, and the volume of sample detected. In a system in which the detection-associated standard deviation between identical samples (coefficient of variance or CV) is small, a very low signal to noise ratio is sufficient to achieve discrimination between a positive result (signal) and a negative result (noise) with a high degree of confidence. Conversely, if a detection system has a high CV, the signal to noise ratio must be greater in order to have the same degree of confidence in the result.

It will also be understood that while reference is made herein to labeled probes, the methods and compositions of the present invention may be practiced in a competition assay format using labeled analyte and unlabeled probe. What is more important is that the probe:analyte complex presents a more favored microenvironment for the label than the hydrophobic interior of the micelles or bilayers, and that they, in turn, present a more favorable microenvironment for the label than the aqueous assay solution.

Moreover, it will also be understood that proteins contain hydrophobic and polar regions, and can form helices. The association of a protein with a probe can result in changes in the microenvironment due to masking or neutralization of one or more of these domains and the creation of three dimensional structures such as pockets and grooves. Thus, in light of the present disclosure, one of skill in the art would reasonably expect that the methods and compositions of the present invention can successfully be used in assays in which the analyte, the probe or both are a protein.

Moreover, where probe and target are both nucleic acids, the target nucleic acid need not necessarily be a single-stranded nucleic acid. For example, Applicant envisions embodiments of the present invention wherein a single standed nucleic acid probe is directed towards a double-standed nucleic acid analyte, resulting in a triple-stranded probe:analyte complex.

Further embodiments of the invention are illustrated in the following examples. These examples do not limit the scope of the present invention, which is defined by the claims which conclude this specification.

EXAMPLES

In the examples the methodology and reagents were as follows, unless indicated to the contrary. Chemical compounds given abbreviations shall be hereafter referred to either by their full name or by their abbreviations. The structures of the following detergents and lipids are depicted in FIG. 2.

A. Amphiphiles

1 Benzylalkonium chloride (BAC) was obtained from Serva Fine Chemicals, Inc., Westbury, N.Y.

2 Benzyldimethyltetradecyl ammonium chloride (BDTAC) was obtained from the Aldrich Chemical Co., Milwaukee, Wis.

3 Benzylcetyldimethyl ammonium chloride (BCDAC) was obtained from the Aldrich Chemical Co., Milwaukee, Wis.

4 Benzyltrimethyl ammonium chloride (BTAC) was obtained from Serva Fine Chemicals, Inc., Westbury, N.Y.

5 Benzyldimethyl stearyl ammonium chloride (BDSAC) was obtained from the Aldrich Chemical Co., Milwaukee, Wis.

6 Benzthonium chloride (BTC) was obtained from Serva Fine Chemicals, Inc., Westbury, N.Y.

7 3-(cyclohexylamino)-2-hydroxyl-1-propane sulfonic acid was obtained from the Sigma Chemical Co., St. Louis, Mo.

8 Cetyltrimethyl ammonium bromide (CTAB) was obtained from Serva Fine Chemicals, Inc., Westbury, N.Y.

9 Cetyl pyridinium bromide (CPB), and was obtained from the Sigma Chemical Co., St. Louis, Mo.

10 Cetyl pyridinium chloride (CPC)was obtained from the Sigma Chemical Co., St. Louis, Mo.

11 Cetyl dimethylethyl ammonium bromide (CDEAB) was obtained from the Sigma Chemical Co., St. Louis, Mo.

12 Brij 35 was obtained from the Sigma Chemical Co., St. Louis, Mo.

13 Tween 20 was obtained from the Sigma Chemical Co., St. Louis, Mo.

14 TRITON® X-100 (TRITON® is a registered trademark of the Union Carbide Chemicals and Plastics Co., Inc.) was obtained from the Kodak Company, Rochester, N.Y.

15 TRITON® X-305 (TRITON® is a registered trademark of the Union Carbide Chemicals and Plastics Co., Inc.) was obtained from the Sigma Chemical Co., St. Louis, Mo.

16 TRITON® Q-S44 (TRITON® is a registered trademark of the Union Carbide Chemicals and Plastics Co., Inc.) was obtained from the Sigma Chemical Co., St. Louis, Mo.

17 Sodium dodecyl sulfate (SDS) was obtained from Biorad Laboratories, San Leandro, Calif.

18 Nonidet P-40 (NP-40) was obtained from the Sigma Chemical Co., St. Louis, Mo.

19 Dioleoyl phosphatidylethanolamine (DOPE)was obtained from where Gibco/BRL, Gaitherburg, Md.

20 Dimethyl dioctadecyl ammonium bromide (DDAB) was obtained from where Gibco/BRL Gaitherburg, Md.

All detergents were dissolved in 0.6 M boric acid (pH 8.8) for use as disclosed in the examples.

B. Labeled Probes

Labels were coupled to the oligonucleotide probes described in the examples using a non-nucleotide linker as described in EPO 0 313 219, supra. For convenience, a single linker type was used for coupling the acridinium ester derivatives to probe in the following examples; this linker was attached at the para position of the phenyl ring and had the formula: phenyl-$(CH_2)_2$—CO—NH—$(CH_2)_5$—CO—NH—$CH_2$—CH— (phosphodiester-nucleotide) —$CH_2$-phosphodiester-nucleotide, where —CH— represents a two-way branch point and one of the two valences are represented by parentheses. Unless indicated to the contrary, the acridinium ester derivative used in each of the Examples was standard AE. All probes labeled with standard AE or AE derivatives had a specific activity of $8 \times 10^{19}$ RLU/mole.

In the examples using rhodamine as a label, the rhodamine was coupled to the oligonucleotide probe in the following manner: a rhodamine conjugate was purchased from Applied Biosystems Inc., (Foster City, Calif.) having an N-hydroxysuccinimide (NHS) group attached thereto (Catalog No. 400980). A 5'dimethoxytrityl-5-[N-trifluoroacetylaminohexyl)-3-acrylimido]-2'-deoxyuridine, 3'-[(2-cyanoethyl)-(N,N-diisopropyl)]-phosphoramidite modified nucleotide was purchased from Glen Research, Sterling, Va. The modified nucleotide was incorporated into the synthetic oligonucleotide; oligonucleotide synthesis was performed using standard phosphoramidite chemistry, see e.g., Carruthers, et al., *Methods in Enzymology*, Volume 143, pg. 287 (1987), Bhatt, U.S. Pat. No. 5,252,723 (which enjoys common ownership with the present invention) and Klem et al., PCT Application No. WO 92/07864, all of which are incorporated by reference herein. The trifluoroacetyl moiety of the modified nucleotide was cleaved with 30% ammonium hydroxide and then reacted with the NHS group of the rhodamine conjugate to then link the rhodamine dye to the nucleotide.

C. Micelle Formation

As indicated above, the detergents were dissolved in 0.6 M sodium borate buffer (pH 8.8) at the concentrations indicated in the examples. One hundred microliters of the resulting solution was placed in a 12 mm×75 mm Sarstedt polystyrene tube for each test point. A 10 μl aliquot of either the hybridized labeled probe and target nucleic acids or the labeled probe alone (50,000–1,000,000 relative light units (RLU) of label; the probes had a specific activity of $8 \times 10^{19}$ RLU/mole) was added to each tube, the tubes vortexed vigorously for 10 seconds, then allowed to sit at room temperature for 10 minutes before the detection step.

D. Detection of Chemiluminescence

Each sample was placed into a Leader® I luminometer (Gen-Probe Incorporated, San Diego, Calif.). Chemiluminescence was initiated by the automated injection into each tube of 200 μl of 0.1% (v/v) $H_2O_2$ in 0.001 N $HNO_3$ followed after 0.5 to 2 seconds by an injection of 200 μl of 1 N NaOH. The resulting chemiluminescence was detected for a total of 5 second per sample.

The following examples illustrate various embodiments of the invention and are intended to fully disclose the general applicability and utility of the methods and compositions and the best mode of the invention presently known to the Applicant. It would be a matter of routine screening for one of ordinary skill in the art to find other charged or neutral surfactants or lipids, combinations of amphiphiles, and conditions which can be used in the methods and compositions of this invention, using the present disclosure as a guide.

Example 1

Figure 3:
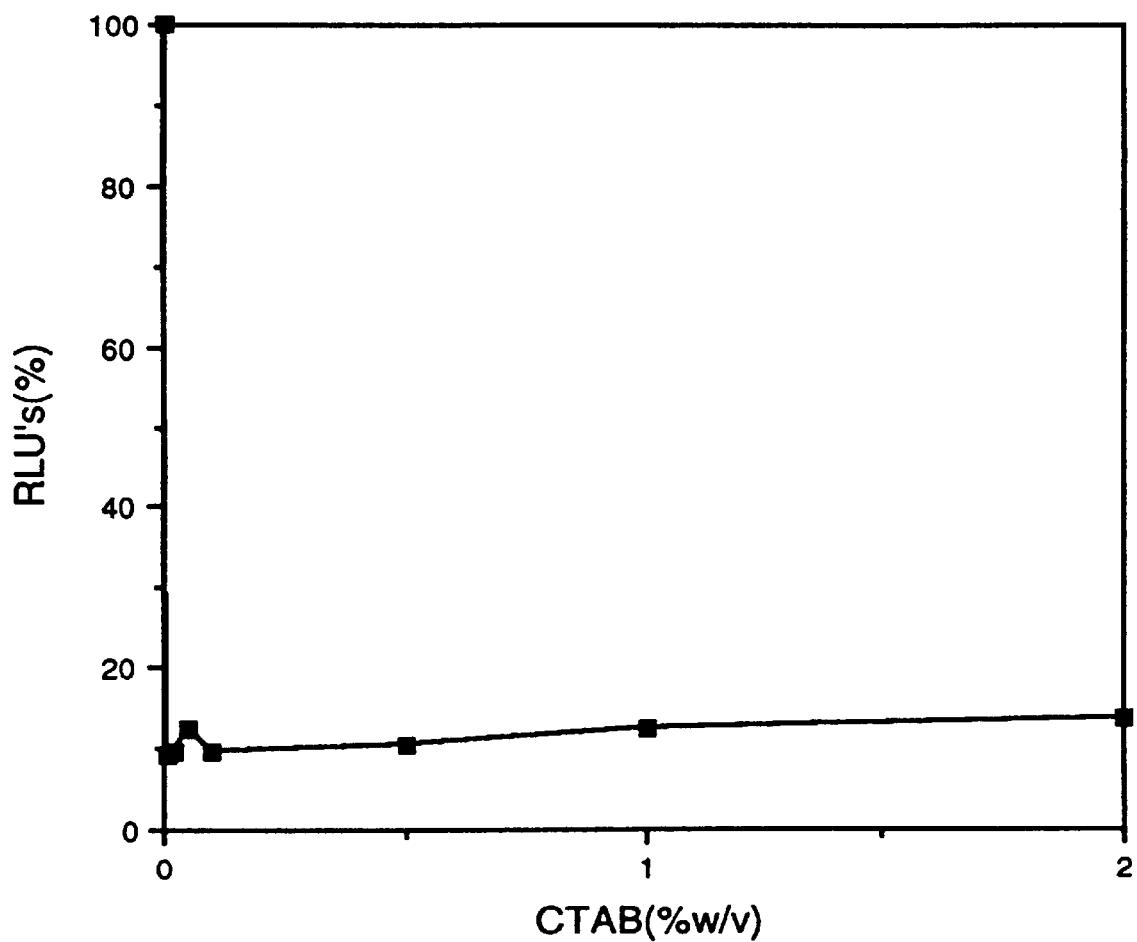
FIG. 3 is a plot of the chemiluminescence of standard AE as a function of CTAB concentration.

In this example, free standard AE (4-(2-succinimidyloxycarbonyl ethyl)-phenyl-10-methylacridinium-9-carboxylate fluorosulfonate) was assayed for chemiluminescence under the following conditions, without being coupled to a probe. Solutions of 100 μl volume and containing 0%, 0.01%, 0.02%, 0.05%, 0.1%, 0.5%, 1% and 2% (w/v) CTAB in 0.6 M sodium borate (pH 8.7) were given 10 μl of a solution of standard AE (approximately 250,000–600,000 RLU; the specific activity of the standard AE used in the examples was $2 \times 10^{20}$ RLU/mole). Micelles were formed as disclosed above. Each sample was then assayed for chemiluminescence in a luminometer as described above. The results are given below and in FIG. 3.

| Tube Number | RLU (percent)* | Concentration CTAB % (w/v) |
|---|---|---|
| 1 | 100.000 | 0.000 |
| 2 | 9.350 | 0.010 |
| 3 | 9.800 | 0.020 |
| 4 | 12.400 | 0.050 |
| 5 | 9.800 | 0.100 |
| 6 | 10.200 | 0.500 |
| 7 | 12.300 | 1.000 |
| 8 | 13.700 | 2.000 |

*100% RLU is the chemiluminescence obtained from the label in the absence of CTAB (258,574 RLU).

The data show that the addition of a low concentration (0.01% (w/v)) of CTAB causes a decrease in the chemiluminescence of free standard AE to about 10% of its chemiluminescent yield in the absence of detergent. This detergent concentration is approximately equal to the critical micelle concentration of 0.026% w/v for CTAB in aqueous solution. At higher concentrations of CTAB the degree of quenching remains high.

Example 2

Figure 4:
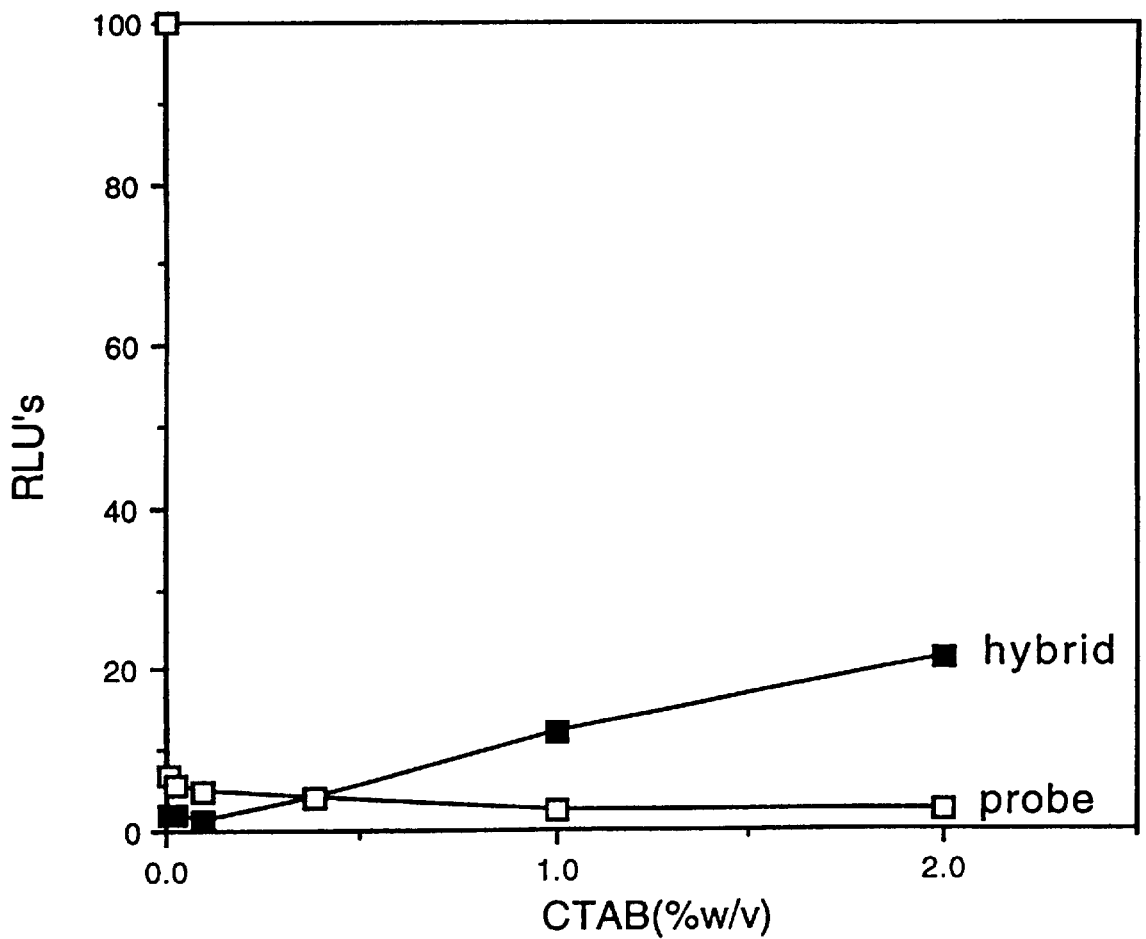
FIG. 4 is a plot of the chemiluminescence or probe-linked and hybrid-linked standard AE as a function of CTAB concentration.

Standard AE was coupled to the probe of SEQ ID NO:7 as described above. In one set of samples 4 μl of the labeled probe (160 pmoles) was added to 8 ml of 11 mM lithium succinate (pH 5.1). One milliliter of this solution was then added to 2 μl (80 pmoles) of the unlabeled DNA target analyte of SEQ ID NO:8 and allowed to hybridize for 40 minutes at room temperature. The other set of samples was treated in exactly the same way but not given the target analyte. As in Example 1, each tube within a set was then given a different concentration of CTAB, and micelles were formed and chemiluminescence detected as described above. The results are given below and in FIG. 4.

| Tube Number | RLU Labeled Hybrid (percent)* | RLU Labeled Probe (percent)* | Concentration CTAB % (w/v) |
|---|---|---|---|
| 1 | 100.000 | 100.000 | 0.000 |
| 2 | 1.900 | 6.600 | 0.010 |
| 3 | 2.000 | 5.800 | 0.030 |
| 4 | 1.300 | 5.000 | 0.100 |
| 5 | 4.000 | 4.100 | 0.380 |
| 6 | 12.250 | 2.400 | 1.000 |
| 7 | 21.200 | 2.600 | 2.000 |

*Percent RLU for labeled probe and labeled hybrid was separately calculated by making the chemiluminescence obtained from each, in the absence of micelles, equal to 100%; thus, 100% RLU for probe = 238,639 and 100% RLU for hybrid = 317,842.

The data indicate that with increasing concentrations of CTAB chemiluminescence is initially decreased to about 3% for the labeled probe and about 3% for the labeled hybrid relative to a control tube having no detergent.

Surprisingly however, as the concentration of CTAB increases the chemiluminescence from the labeled hybrid increases to about 20% of its initial value (in the absence of detergent) while the chemiluminescent yield from tubes containing labeled probe alone decreases under the same conditions. Thus, these results demonstrate that the presence of the DNA target analyte can be detected in a homogeneous assay format using CTAB alone, due to the ability of the assay system to discriminate between hybrid-associated, detectable label and probe-associated, quenched label at concentrations above about 0.38% (w/v) CTAB.

Example 3

In this example, all tubes contained 0.4% (w/v) CTAB in 0.6 M sodium borate. As shown in the previous example this is the concentration of CTAB at which there is little or no discrimination between labeled probe and labeled probe/analyte hybrid (see FIG. 4).

Three sets of tubes were made as in Example 2; one set contained only the free AE label, another set of tubes contained the labeled probe alone, and a third set of tubes contained the labeled probe:DNA analyte hybrid. Hybridization was performed as described in Example 2. The probe and target oligonucleotides were those used in Example 2. Tubes within each set were also given TRITON® X-100 (polyethylene glycol p-isooctylphenyl ether; also in 0.6 M sodium borate) to a final concentration of 0%, 0.5%, 1%, 2% and 4% (v/v). Micelle formation and detection of chemiluminescence was performed as described in Example 1 (free label) and Example 2 (labeled probe and labeled probe:analyte hybrid).

Figure 5:
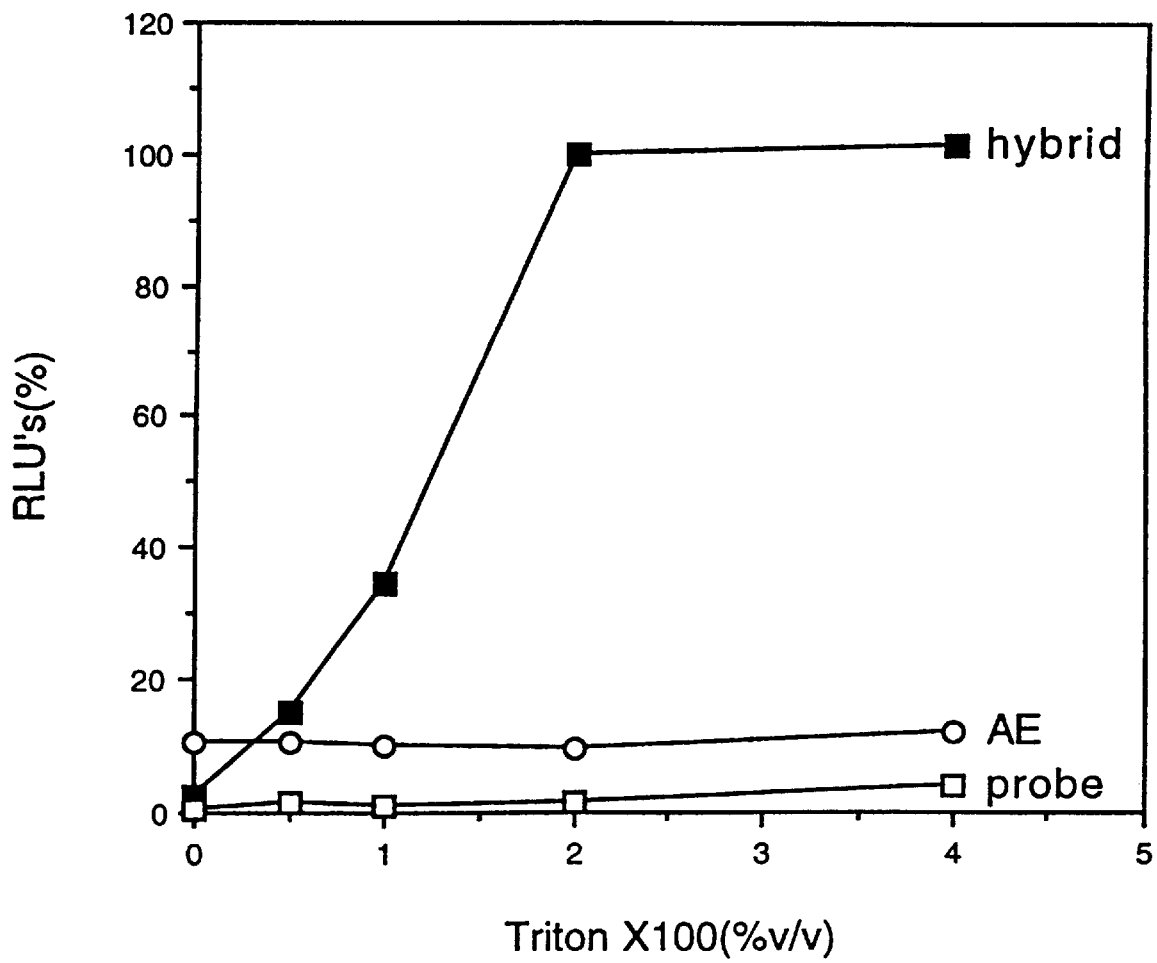
FIG. 5 is a plot of the chemiluminescence of free standard AE, probe-linked standard AE, and hybrid-linked standard AE, in the presence of CTAB, as a function of TRITON X-100 concentration.

As shown below and in FIG. 5, the addition of TRITON® X-100 to form mixed micelles of detergents having different hydrophobic "tails" had little effect on the chemiluminescent yield of the free AE label and the AE labeled probe, with the former maintaining a chemiluminescent yield of about 10% of the "no surfactant" control and the latter having an even lower yield across the range of TRITON® X-100 concentrations tested.

Surprisingly however, the chemiluminescent signal obtained from the labeled probe:analyte hybrid increased drastically at concentrations within the range of 0% and 2% (v/v) of added TRITON® X-100; from about 2% to about 100% of the RLUs obtained in the absence of any detergent. Thus, the ability of the assay to discriminate between labeled hybrid and labeled probe is substantially increased when mixed micelles are used. While Applicants remain uncertain as to the precise mechanism by which this discrimination is enchanced in the presence of mixed micelles, these data and the additional data presented below strongly suggest that changing the hydrophobicity of the micelle interior by mixing amphiphiles having different "tails" can increase the micelles' ability to sequester the label linked to the free probe over that associated with the probe:analyte complex.

| Tube Number | Concentration TRITON ® X-100% (v/v) | RLU Labeled Probe (percent)* | RLU Labeled Hybrid (percent)* | RLU Standard AE (percent)* |
|---|---|---|---|---|
| 1 | 0.000 | 0.610 | 2.500 | 10.600 |
| 2 | 0.500 | 1.330 | 15.200 | 10.550 |
| 3 | 1.000 | 1.030 | 34.800 | 10.220 |
| 4 | 2.000 | 1.500 | 100.000 | 9.740 |
| 5 | 4.000 | 4.000 | 101.300 | 11.900 |

*100% RLU is assigned to the chemiluminescence obtained from each of the standard AE, labeled probe, and labeled hybrid conditions in the absence of micelles. 100% (uncoupled standard AE) = 258,574, 100% (labeled probe) = 606,625 and 100% (labeled hybrid) = 613,519.

Example 4

Micelles made from another positively charged surfactant, cetylpyridinium chloride (CPC), were tested for their ability to cause discrimination between AE-labeled probe and AE-labeled hybrid. CPC has the same hydrophobic side chain as CTAB but a different polar "head" group. Two sets of samples were used, one using the labeled probe:DNA target analyte hybrids (hybridized as in Example 2) and the other using only the labeled probe. Probe and target oligonucleotides were those used in Example 2 above. For each set of tubes, solutions of 0.01%, 0.1%, 0.3%, 0.5%, and 1% (w/v) CPC were made. The micelle formation and detection steps were as described above.

Figure 6:
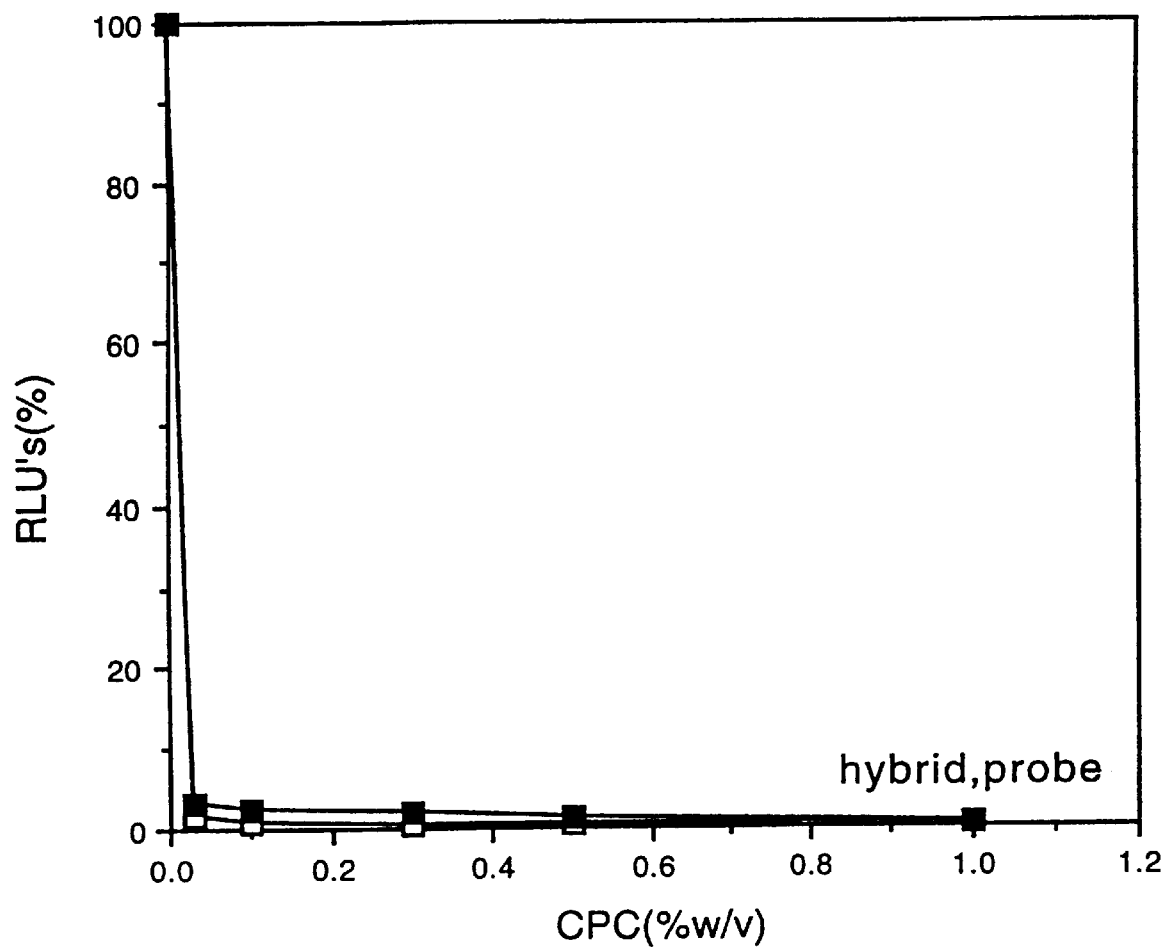
FIG. 6 is a plot of the chemiluminescence or probe-linked and hybrid-linked standard AE as a function of CPC concentration.

As shown below and in FIG. 6, the chemiluminescence of both the labeled probe and labeled hybrid was strongly quenched even at 0.01% CPC, and the quenching effect grew in both cases until almost no light was emitted from either sample at a concentration of 1% (w/v) CPC.

| Tube Number | RLU (labeled probe) (percent)* | RLU (labeled hybrid) (percent)* | Concentration CPC % (w/v) |
|---|---|---|---|
| 1 | 100.000 | 100.000 | 0.000 |
| 2 | 1.440 | 3.360 | 0.030 |
| 3 | 0.960 | 2.400 | 0.100 |
| 4 | 0.450 | 2.050 | 0.300 |
| 5 | 0.380 | 1.340 | 0.500 |
| 6 | 0.490 | 0.600 | 1.000 |

*100% RLU is assigned to the chemiluminescence obtained from each of the labeled probe and labeled hybrid conditions in the absence of CPC. 100% (labeled probe) = 206,968 RLU and 100% (labeled hybrid) = 316,803 RLU.

Example 5

In this example, the effect of the charged surfactant's counter-ion on the degree of discrimination was tested by forming micelles containing either 0.4% CPC or CPB and varying the concentration of TRITON® X-100. The only difference between these compounds is that the counter-ion in the former is chloride and the counter-ion in the latter is bromide. The probe and target oligonucleotides were those used in Example 2.

Four sets of tubes were made up: two contained the free probe coupled to standard AE in either 0.4% (w/v) CPC or CPB, and two contained the labeled probe:DNA target hybrid in either of the two cationic surfactants. Each set of tubes was given 0%, 0.5%, 1%, 2% and 4% (v/v) TRITON® X-100. Hybridization, micelle formation and detection were as described in Example 2 above.

Figure 7:
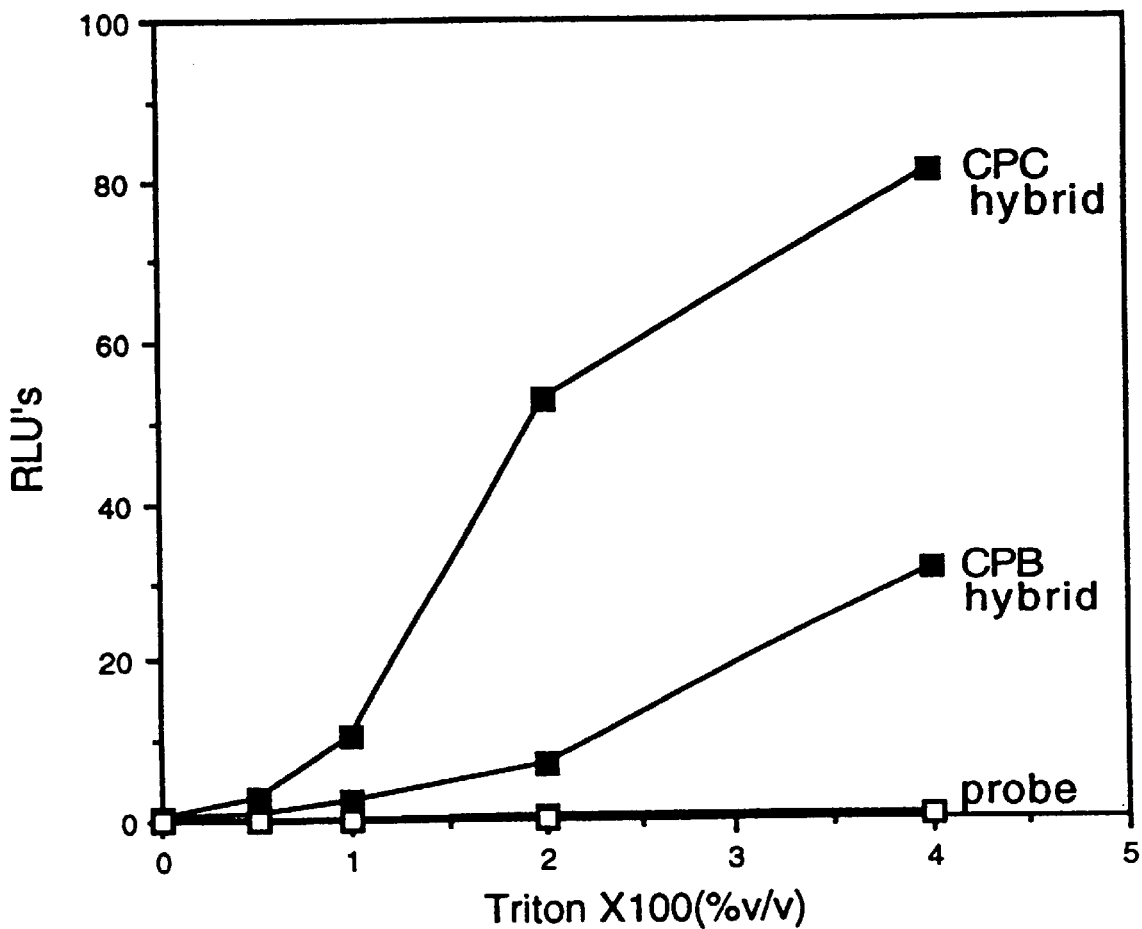
FIG. 7 is a plot of the chemiluminescence of probe-linked or hybrid-linked standard AE, in the presence of CPC or CPB, as a function of TRITON X-100 concentration.

As shown below and in FIG. 7, the chemiluminescence of the labeled probe alone was similarly strongly quenched regardless of the nature of the counter-ion. By contrast however, the chemiluminescence of the labeled hybrid in CPC was less quenched with increasing concentrations of TRITON® X-100 than was the labeled hybrid in CPB, with the 0.4% (w/v)CPC/4% (v/v) TRITON® X-100 mixed micelles returning the detectability of the AE-labeled hybrid to about 81% of its value in the absence of any detergent and the 0.4% (w/v) CPB/4% (v/v) TRITON® X-100 mixed micelles restoring only about 36% of the same value.

| Tube Number | RLU (labeled hybrid in CPC) (percent)* | RLU (labeled probe in CPC) (percent)* | RLU (labeled hybrid in CPB) (percent)* | RLU (labeled probe in CPB) (percent)* | Concentration TRITON ® X-100% (v/v) |
|---|---|---|---|---|---|
| 1 | 0.270 | 0.080 | 0.330 | 0.080 | 0.000 |
| 2 | 2.700 | 0.100 | 0.990 | 0.090 | 0.500 |
| 3 | 10.400 | 0.120 | 2.260 | 0.120 | 1.000 |
| 4 | 53.000 | 0.210 | 6.960 | 0.170 | 2.000 |
| 5 | 81.000 | 0.390 | 31.600 | 0.400 | 4.000 |

*100% RLU is assigned to the chemiluminescence obtained from each of the labeled probe and labeled hybrid conditions in the absence of micelles. 100% (labeled hybrid) = 602,982 RLU and 100% (labeled probe) = 579,711 RLU.

The data show that the nature of the hydrophobic "tails" of detergents comprising mixed micelles is not the sole factor affecting discrimination between labeled probe:analyte conjugate and labeled free probe; although the hydrophobicity of the two sets of mixed micelles tested in this example was presumably identical, discrimination was affected by the counterion associated with the charged detergent. The data also show that, irrespective of the charged detergent used, addition of TRITON® X-100 allows differentiation between the free probe and hybrid. Lastly, these results suggest that discrimination is enhanced under these conditions by decreasing the hydrophobicity of the micelle interior by the addition of TRITON® X-100.

Example 6

Figure 8:
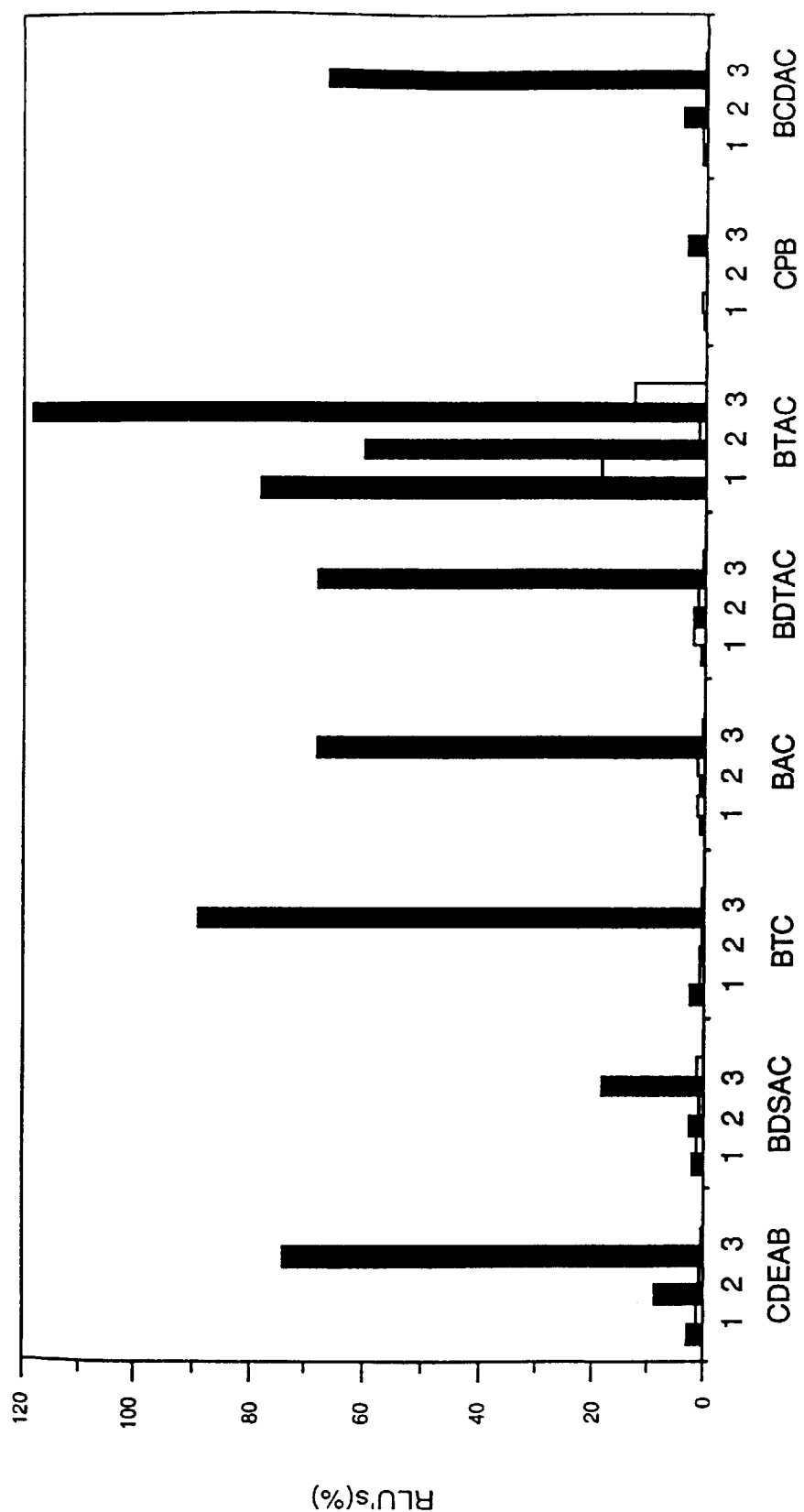
FIG. 8 is a graph showing the effect of different cationic detergents on the chemiluminescence of probe-linked and hybrid-linked standard AE.

A panel of cationic detergents was evaluated for use in conjunction with the methods of the present invention; the detergents tested were CDEAB, BDSAC, BTC, SAC, BDTAC, BTAC, CPB and BCDAC. Each detergent was disolved in 0.6 M sodium borate (pH 8.7). For each detergent the detectability of free AE-labeled probe and the labeled DNA hybrid was determined under three conditions: a) in the presence of 0.05% (w/v) cationic surfactant, b) in the presence of 0.5% (w/v) cationic surfactant, and c) in the presence of 0.5% (w/v) cationic surfactant plus 2% (v/v) TRITON® X-100. Hybridization was as described in Example 2. The micelle formation and detection steps were conducted as described above. Probe and target oligonucleotides were those used in Example 2. The results are shown below and in FIG. 8.

The results demonstrate the general applicability of the presently disclosed method. As can be clearly seen, some of the detergents are able to differentiate between probe-linked standard AE and hybrid-linked standard AE in the absence of added TRITON® X-100 (i.e., BTAC), while other detergents are better able to discriminate when present in mixed micelles with TRITON® X-100 (i.e., CDEAB, BDSAC, BTC, BAC, BDTAC, and BCDAC). In all cases the detergent micelles inhibit the chemiluminescent detectability of the unhybridized labeled probe to a greater degree than they inhibit the detectability of the labeled hybrid resulting in discrimination between hybrid and probe. Indeed, at least in the case of BTAC, the chemiluminescent yield of the labeled hybrid appears to be enhanced in the presence of mixed micelles when assayed under these conditions.

| Cationic Detergent | 0.05% (w/v) Cationic Detergent | | 0.5% (w/v) Cationic Detergent | | 0.5% (w/v) Cationic Detergent + 2% TRITON ® X-100 | |
|---|---|---|---|---|---|---|
| | RLU (labeled hybrid) (percent)* | RLU (labeled probe) (percent)* | RLU (labeled hybrid) (percent)* | RLU (labeled probe) (percent)* | RLU (labeled hybrid) (percent)* | RLU (labeled probe) (percent)* |
| CDEAB | 2.900 | 1.460 | 8.500 | 0.890 | 74.000 | 0.420 |
| BDSAC | 1.850 | 1.580 | 2.300 | 1.000 | 18.400 | 1.300 |
| BTC | 2.200 | 1.060 | 1.030 | 0.580 | 89.050 | 0.410 |
| BAC | 1.060 | 1.170 | 1.170 | 1.510 | 68.300 | 0.650 |
| BDTAC | 1.160 | 1.710 | 1.810 | 1.330 | 68.100 | 0.390 |
| BTAC | 78.200 | 18.800 | 60.100 | 1.620 | 118.000 | 13.300 |
| CPB | 0.500 | 0.960 | 0.125 | 0.180 | 3.230 | 0.160 |
| BCDAC | 1.060 | 0.930 | 4.330 | 0.590 | 67.000 | 0.520 |

*100% RLU is assigned to the chemiluminescence obtained from each of the labeled probe and labeled hybrid conditions in the absence of micelles. 100% (labeled hybrid) = 395,580 RLU and 100% (labeled probe) = 389,611 RLU.

Example 7

The ability of homogeneous, uncharged micelles containing only TRITON® X-100 to discriminate between labeled probe and labeled probe:analyte hybrid was examined in the following way. Either AE-labeled probe or AE-labeled probe:analyte hybrid were given TRITON® X-100 to a final concentration of 0%, 0.03%, 0.1%, 0.5%, 2% or 4% (v/v). Hybridization, micelle formation and detection were performed as in Example 2. Probe and target oligonucleotides were those used in Example 2.

Figure 9:
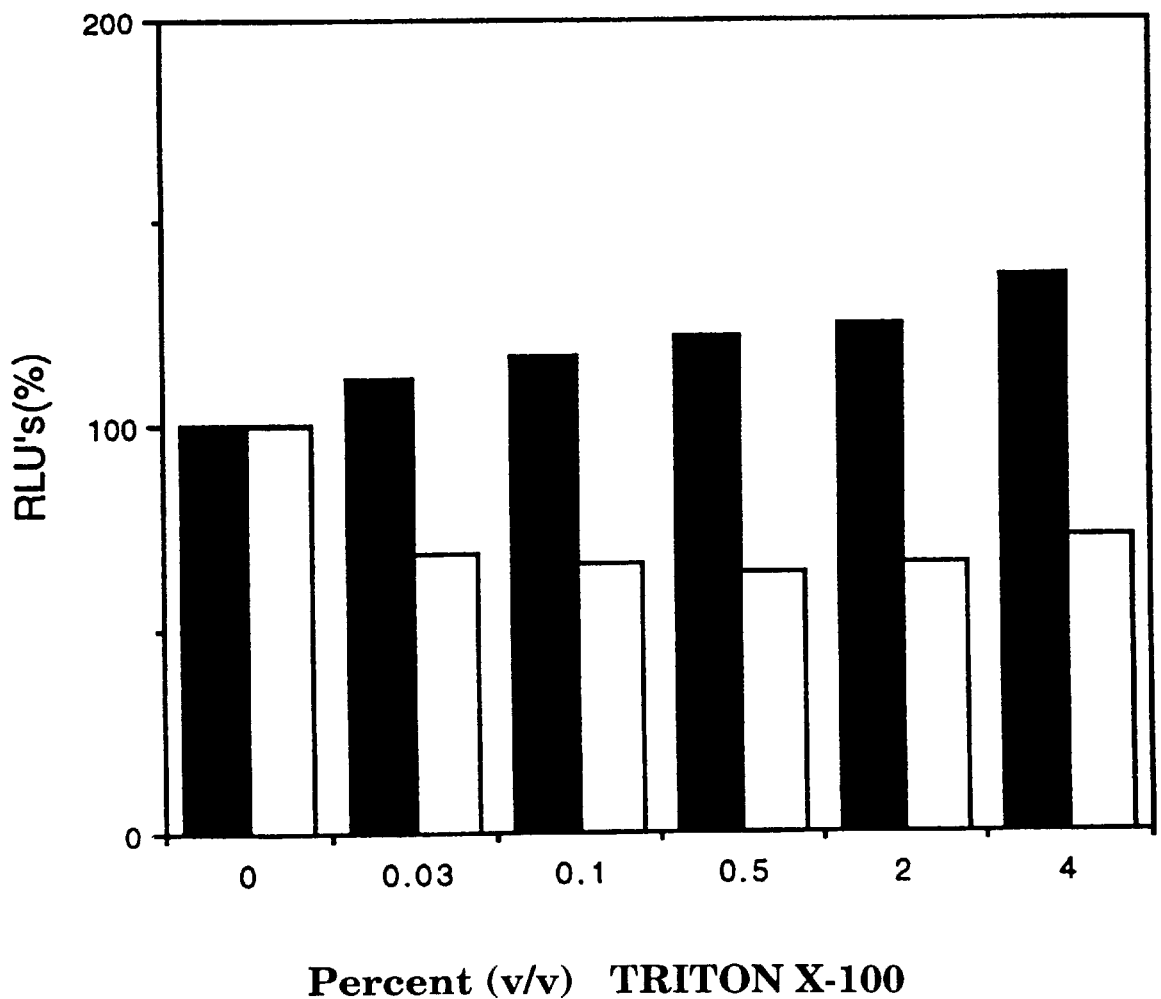
FIG. 9 is a graph showing the effect of increasing amounts of TRITON X-100 on the chemiluminescence of probe-linked and hybrid-linked standard AE.

As shown below and in FIG. 9, with the addition of even a small amount (0.03%) of TRITON® X-100 to the solutions discrimination between probe and hybrid was clearly demonstrated. With increasing concentrations of TRITON® X-100 the chemiluminescence of the hybrid-associated label continued to increase, while the quenching effect of the micelles on the labeled probe alone appeared to be minimized between concentrations of about 0.5% to 2% TRITON® X-100. Thus, this experiment demonstrates that assays employing the present invention using homogeneous non-ionic detergent micelles are able to discriminate between probe and hybrid.

| Concentration (v/v) TRITON ® X-100 | RLU (labeled hybrid in TRITON ® X-100) (percent)* | RLU (labeled probe in TRITON ® X-100) (percent)* |
| --- | --- | --- |
| 0 | 100 | 100 |
| 0.03 | 111 | 68 |
| 0.1 | 117 | 66 |
| 0.5 | 122 | 63 |
| 2 | 125 | 66 |
| 4 | 137 | 72 |

*100% RLU is assigned to the chemiluminescence obtained from each of the labeled probe and labeled hybrid conditions in the absence of micelles. 100% (labeled hybrid) = 318,550 RLU and 100% (labeled probe) = 273,953 RLU.

Example 8

Figure 10:
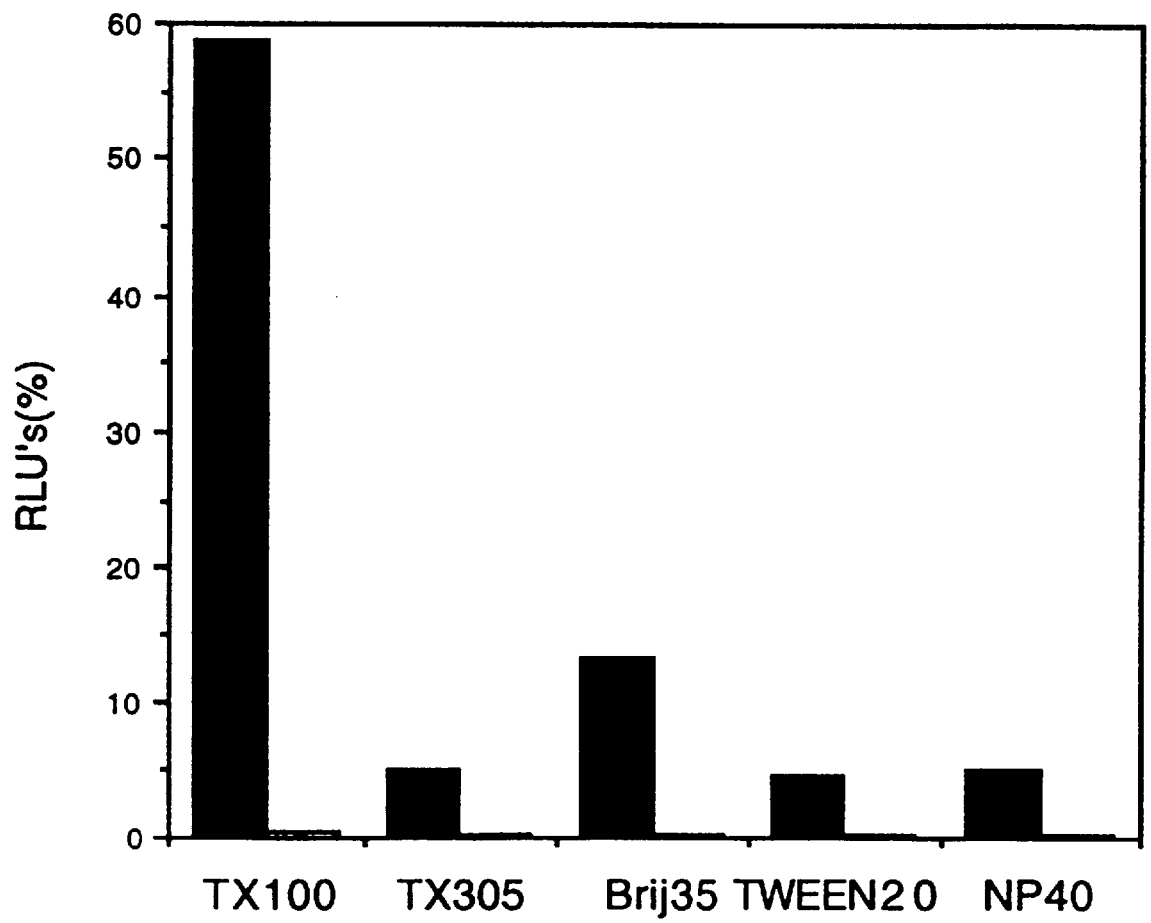
FIG. 10 is a graph showing the effect of mixed micelles containing CPC and different neutral detergents on the chemiluminescence of probe-linked and hybrid-linked standard AE.

A panel of neutral detergents was evaluated for use conjunction with the methods of the present invention in mixed micelles with CPC. The neutral detergents tested were TRITON® X-100, TRITON® X-305, Brij 35, Tween 20, and NP-40. For each neutral detergent the detectability of free AE-labeled probe and the labeled DNA hybrid was determined in the presence of 0.4% (w/v) CPC and 2% (v/v) of the neutral detergent. Hybridization, micelle formation and detection steps were conducted as described in Example 2. Probe and target oligonucleotides were those used in Example 2. The results are given below and in FIG. 10.

| Ionic Detergent | RLU (labeled probe) (percent)* | RLU (labeled hybrid) (percent)* |
| --- | --- | --- |
| TRITON ® X-100 | 0.450 | 58.800 |
| TRITON ® X-305 | 0.210 | 5.000 |
| Brij 35 | 0.350 | 13.200 |
| Tween 20 | 0.280 | 4.700 |
| NP-40 | 0.320 | 5.200 |

*100% RLU is assigned to the chemiluminescence obtained from each of the labeled probe and labeled hybrid conditions in the absence of micelles. 100% (labeled hybrid) = 578,863 RLU and 100% (labeled probe) = 556,523 RLU.

Under these uniform assay conditions, mixed micelles formed from CPC and each of the evaluated neutral detergents were able to discriminate between AE-labeled probe and AE-labeled DNA hybrid.

Example 9

Figure 11:
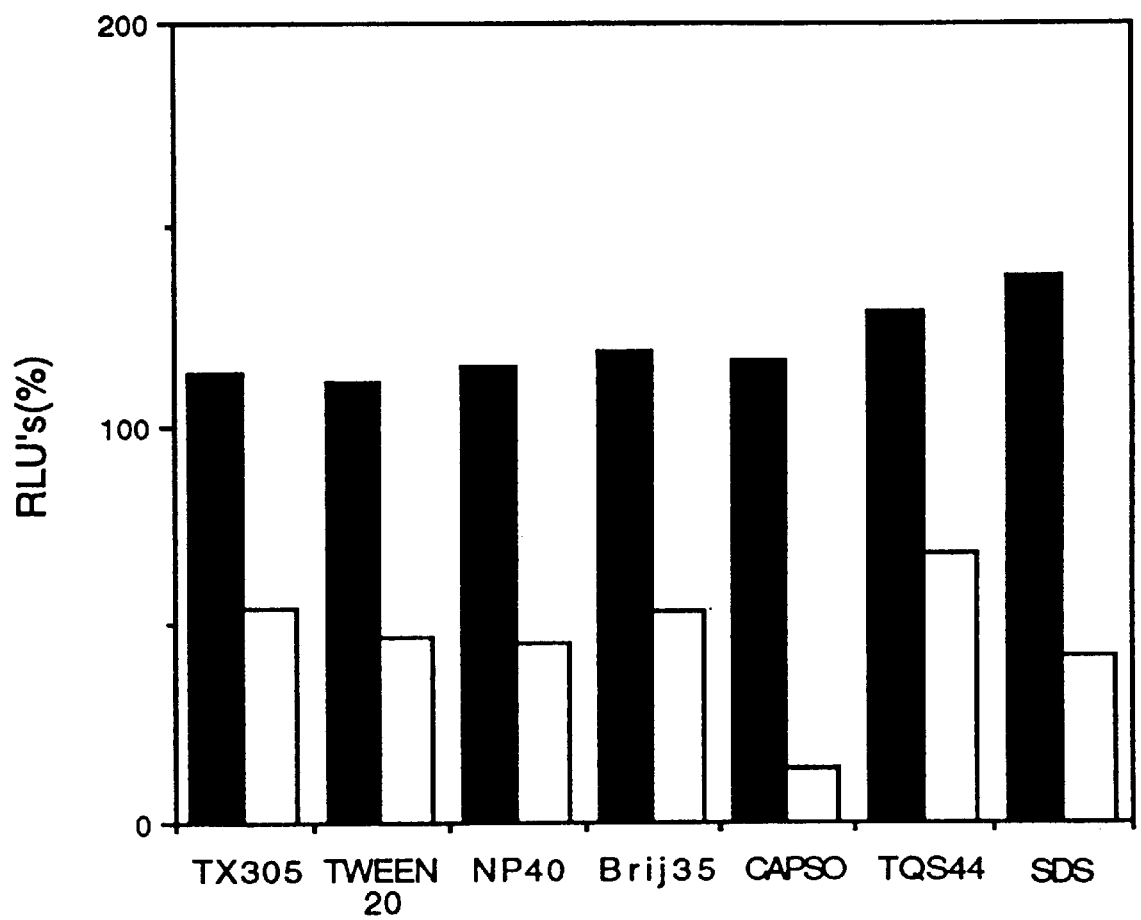
FIG. 11 is a graph showing the effect of homogeneous micelles composed of cationic, anionic and zwitterionic detergents on the chemiluminescence of probe-linked and hybrid-linked standard AE.

A panel of different surfactants was evaluated for use in the methods of the present invention. In this example, homogeneous micelles formed solely of each of the evaluated surfactants were used. These surfactants were neutral (TRITON® X-305, Brij 35, Tween 20, and NP-40) zwitterionic (CAPSO) and anionic (TRITON® QS-44 and sodium dodecyl sulfate (SDS)) in nature. 0.5% (v/v) of each detergent was used except in the case of Brij 35, CAPSO and SDS, where 0.5% (w/v) was used. Micelle formation and detection of the standard AE label was otherwise as described in Example 1. The probe and target oligonucleotides were those used in Example 2. The results are given below and illustrated in FIG. 11.

| Detergent | RLU (labeled probe) (percent)* | RLU (labeled hybrid) (percent)* |
| --- | --- | --- |
| TRITON ® X-305 | 54.000 | 114.000 |
| Tween 20 | 47.000 | 111.000 |
| NP-40 | 45.000 | 115.000 |
| Brij 35 | 53.000 | 119.00 |
| CAPSO | 14.000 | 117.00 |
| TRITON ® QS-44 | 68.000 | 129.000 |
| SDS | 42.000 | 138.000 |

*100% RLU is assigned to the chemiluminescence obtained from each of the labeled probe and labeled hybrid conditions in the absence of micelles. 100% (labeled hybrid) = 318,550 RLU and 100% (labeled probe) = 273,950 RLU.

As the data demonstrate, anionic, neutral and zwitterionic micelles are capable of preferentially quenching the chemiluminescence of the unhybridized probe-coupled label over that of the hybrid-coupled label in a fashion similar to that seen for cationic micelles. However, the magnitude of discrimination observed is less than that seen with cationic micelles presumably due to the lack of ionic interaction between the negatively charged nucleic acid and the detergent.

Example 10

Figure 12:
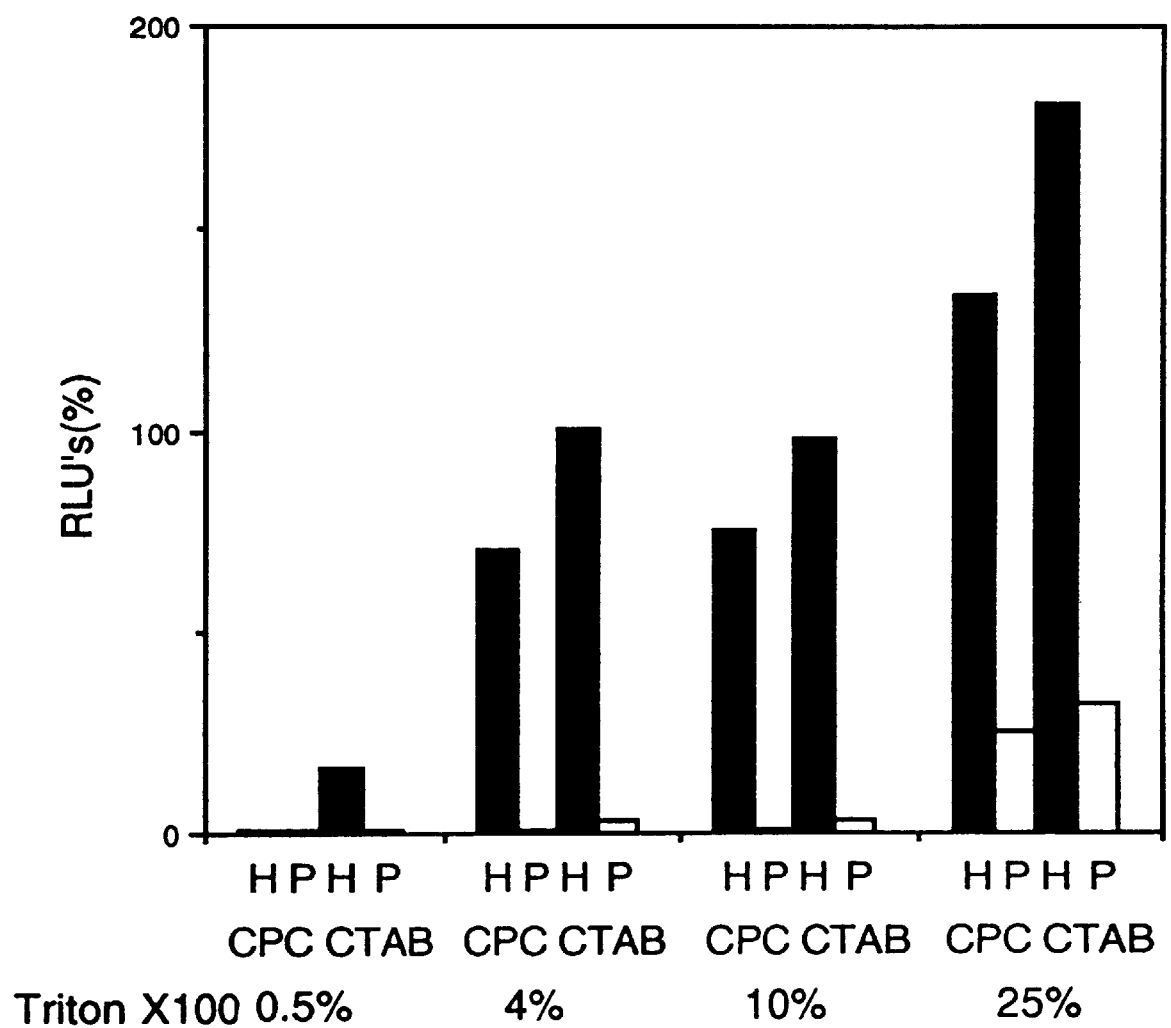
FIG. 12 is a graph showing the effect of mixed micelles containing fixed concentrations of CPC or CTAB and increasing concentrations of TRITON X-100 on the chemiluminescence of probe-linked and hybrid-linked standard AE.

The effect of high concentrations of TRITON® X-100 on label discrimination was determined under conditions of constant concentration of cationic detergent. Two cationic surfactants, CPC and CTAB, were used in these examples; both were present at a concentration of 0.4% (w/v). TRITON® X-100 was added to the tubes of each set (containing either CPC or CTAB) at concentrations of 0.5%, 4%, 10%, and 25% (v/v). Hybridization was performed as in Example 2; micelle formation and detection steps were as in Example 1. The probe and target oligonucleotides were those used in Example 2. The results are shown below and in FIG. 12.

| Concentration TRITON ® X-100 % (w/v) | CPC | | | CTAB | | |
| --- | --- | --- | --- | --- | --- | --- |
| | RLU (labeled hybrid) percent* | RLU (labeled probe) percent* | % hybrid — % probe | RLU (labeled hybrid) percent* | RLU (labeled probe) percent* | % hybrid — % probe |
| 0.5% | 1.200 | 0.500 | 2.4 | 16.500 | 0.750 | 22 |
| 4% | 70.000 | 1.000 | 70 | 101.000 | 3.200 | 3.44 |

-continued

| Concent-ration TRITON ® X-100 % (w/v) | CPC | | | CTAB | | |
|---|---|---|---|---|---|---|
| | RLU (labeled hybrid) percent* | RLU (labeled probe) percent* | % hybrid — % probe | RLU (labeled hybrid) percent* | RLU (labeled probe) percent* | % hybrid — % probe |
| 10% | 75.000 | 1.000 | 75 | 98.000 | 3.000 | 32.67 |
| 25% | 134.000 | 25.000 | 5.36 | 181.000 | 32.000 | 5.66 |

*100% RLU is assigned to the chemiluminescence obtained from each of the labeled probe and labeled hybrid conditions in the absence of micelles. 100% (labeled hybrid) = 575,566 RLU and 100% (labeled probe) = 558,255 RLU.

The data show that increasing the concentration of TRITON® X-100 from 0.5% to 4% (v/v) (and thus the ratio of TRITON® X-100 to ionic surfactant comprising the mixed micelles) increases the chemiluminescent yield of the standard AE-labeled hybrid while not greatly decreasing the quenching of the labeled, unhybridized probe. This is true whether the ionic detergent is CPC or CTAB (both of which have identical hydrophobic "tails" which differ from the hydrophobic "tail" of TRITON® X-100), although the chemiluminescent yield of the standard AE-labeled hybrid in a solution having CTAB-containing micelles was consistently greater than in the CPC system under these conditions. The results are nearly identical when the concentration of TRITON® X-100 is raised to 10% (v/v). At a TRITON® concentration of 25% (v/v) the chemiluminescent yields of the labeled hybrid are enhanced above that seen for detection of the hybrid in a system not containing surfactant micelles; however the quenching of the labeled probe is significantly decreased leading to greater background and a diminution of the signal-to-noise ratio (% hybrid/% probe) for the assay.

Example 11

Figure 13:
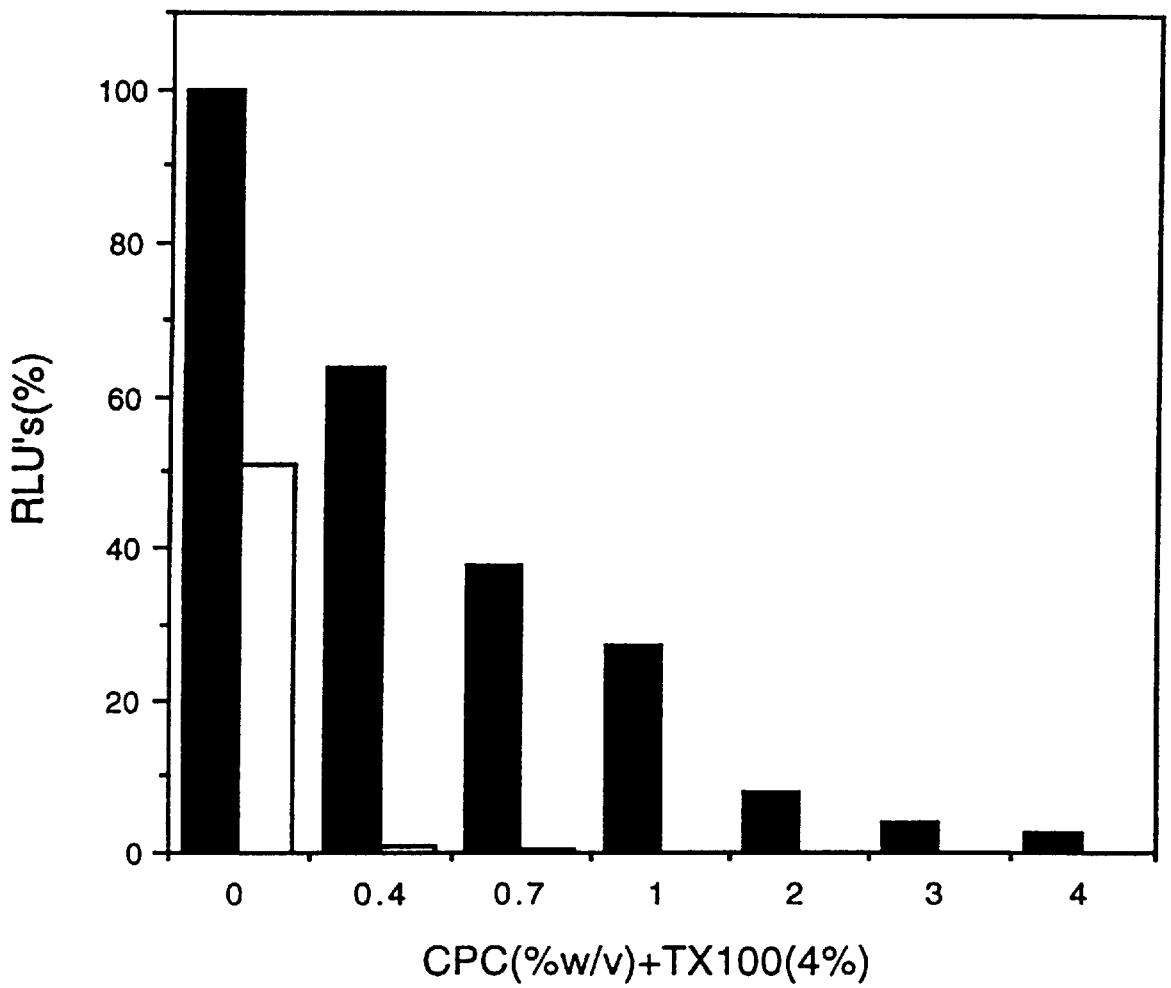
FIG. 13 is a graph showing the effect of mixed micelles containing fixed concentrations of TRITON X-100 and increasing concentrations of CPC on the chemiluminescence of probe-linked and hybrid-linked standard AE.

The effect on label discrimination of raising the concentration of ionic surfactant was measured under conditions of a constant concentration of TRITON® X-100. The concentration of TRITON® X-100 in each tube was 4% (v/v). Two sets of tubes containing increasing concentrations (0%, 0.4%, 0.7%, 1%, 2%, 3%, and 4% (w/v)) of CPC were made; one contained the AE-labeled probe alone, the other contained the AE-labeled hybrid. The probe and target oligonucleotides were those used in Example 2. Hybridization was as described in Example 2; micelle formation and detection was as described in Example 1. The results were as shown below and in FIG. 13.

| Tube Number | Concentration CPC % (w/v) | RLU (labeled hybrid) (percent)* | RLU (labeled probe) (percent)* | % hybrid — % probe |
|---|---|---|---|---|
| 1 | 0.000 | 100.000 | 51.000 | 1.96 |
| 2 | 0.400 | 64.000 | 0.700 | 91.4 |
| 3 | 0.700 | 38.000 | 0.230 | 165.2 |
| 4 | 1.000 | 27.400 | 0.070 | 391.4 |
| 5 | 2.000 | 8.000 | 0.090 | 88.9 |

-continued

| Tube Number | Concentration CPC % (w/v) | RLU (labeled hybrid) (percent)* | RLU (labeled probe) (percent)* | % hybrid — % probe |
|---|---|---|---|---|
| 6 | 3.000 | 4.000 | 0.000 | — |
| 7 | 4.000 | 2.600 | 0.055 | 47.3 |

*100% RLU is assigned to the chemiluminescence obtained from each of the labeled probe and labeled hybrid conditions in the absence of micelles. 100% (labeled hybrid) = 605,316 RLU and 100% (labeled probe) = 307,205 RLU.

As the results indicate, when no CPC is added to the system, the mount of chemiluminescence detected due to labeled free probe is about 50% of that detected for the labeled hybrid (yielding a signal-to-noise ratio of about 2:1). Upon addition of CPC at a concentration of 0.4% (w/v), however the signal-to-noise ratio is increased to about 91:1. At a CPC concentration of 0.7% the signal-to-noise ratio is increased to 165:1; at CPC concentrations above 1% (w/v) there is no significant improvement of signal-to-noise ratio. Under these conditions, therefore, a relatively low concentration of the ionic surfactant is sufficient to obtain good discrimination between labeled hybrid and free probe without sacrificing significant assay sensitivity. These data demonstrate the importance of obtaining a proper mix of different detergents in the mixed micelles of the present invention in order to maximize discrimination between free probe and probe:analyte conjugate; screening experiments such as this and others provided in the examples would be routine for one of skill in the art, and are applicable to any combination of label and amphiphile.

Example 12

The ability of the present invention to be used in conjunction with and enhance the performance of other assay methodologies is demonstrated. In this example, standard AE-labeled probes and hybrids were evaluated using the hybridization protection assay (HPA), either in the absence or in the presence of the surfactant micelles described herein. The HPA described in Arnold et al., U.S. Pat. No. 5,283,174, incorporated herein by reference, makes use of a differential hydrolysis method to discriminate between a labeled analyte:probe complex and a labeled probe. However a small amount of the probe-associated label is resistant to hydrolysis, which can contribute to background chemiluminescence.

Two different DNA probe/analyte pairs were evaluated in this example. The first probe and target oligonucleotides were of SEQ ID NOs: 5 and 6, respectively. The second probe and target were of SEQ ID NOs: 3 and 4, respectively.

Each probe was coupled to standard AE by the methodology described above.

Hybridization reactions were conducted as follows: 1 μl (1 pmole) of probe was added to 30 μl of 0.5 M LiCl, 0.1 M lithium succinate (pH 5.1). To tubes representing probe:analyte hybrid was also added 4 μl target analyte (4 pmole). The tubes were incubated at 60° C. for 30 minutes.

Three conditions were established for pairs of tubes containing either labeled DNA probe or labeled DNA hybrid. The oligonucleotides (either labeled probe alone or labeled hybrid) were added to 100 μl 0.6M sodium borate (pH 8.7) and 1% (v/v) TRITON® X-100 and the free probe-associated label was allowed to hydrolyze by incubation at 60° C. for 10 minutes. Aliquots of the pre- and post-hydrolysis mixture were taken for detection. For the samples to which micelles were to be added, the tubes were then given 100 μl 0.8% (w/v) CPC, 6% (v/v) TRITON® X-100 and 0.6M sodium borate (pH 8.7) (SEQ ID NOS:5 and 6) or 0.8% (w/v) CPC, 4% (v/v) TRITON® X-100 and 0.6M sodium borate (pH 8.7) (SEQ ID NOS:3 and 4); the same solutions minus TRITON® X-100 were added to the aliquots already collected. Micelle formation and detection was as in Example 1. The results are shown below:

| Probe & Target Oligonucleotides | RLU (labeled probe) | RLU (labeled hybrid) | Blank | % Probe | % Hybrid | % Hybrid — % Probe |
|---|---|---|---|---|---|---|
| SEQ ID NOS: 5 & 6 (No micelle) | 659690 | 937988 | 360 | 100 | 100 | 1 |
| SEQ ID NOS: 5 & 6 (HPA) | 1249 | 332084 | 360 | 0.0135 | 35.4 | 2622 |
| SEQ ID NOS: 5 & 6 (HPA and micelle) | 790 | 212796 | 552 | 0.0036 | 22.6 | 6278 |
| SEQ ID NOS: 3 & 4 (No micelle) | 7335130 | 914096 | 336 | 100 | 100 | 1 |
| SEQ ID NOS: 3 & 4 (HPA) | 1369 | 596856 | 336 | 0.0141 | 65.3 | 4631 |
| SEQ ID NOS: 3 & 4 (UPA and micelle) | 698 | 324046 | 572 | 0.0017 | 35.4 | 20824 |

*100% RLU is assigned to the chemiluminescence obtained from each of the labeled probe and labeled hybrid conditions in the absence of micelles.

As can be clearly seen in the data obtained using each probe:target combination, the signal-to-noise ratio of the assay, determined by comparing the chemiluminescence detected from the labeled hybrid with the chemiluminescence detected from the free labeled probe, is improved using the methods of the present invention. In one case the increase in the signal-to-noise ratio for the micelle-containing assay was 2.4 times the signal-to-noise ratio observed for the same assay without micelles; in the assay using the other probe and analyte pair the signal-to-noise ratio was about 4.5 times greater than that observed in the non-micelle-containing assay. Thus, the results indicate the general utility of the present invention in increasing the signal-to-noise ratio of other assay systems when used in conjunction therewith. Also, experiments such as these have shown that the variation between replicate samples in assays employing differential hydrolysis of AE-labeled probes is decreased using amphiphiles as described herein, thus improving the precision of the assay and the degree of confidence of the quantitative results.

Example 13

In this experiment the ability of the present invention to discriminate between labeled probe and a labeled DNA:RNA hybrid was evaluated. The target nucleic acid was whole ribosomal RNA (rRNA) purified from a pure culture of Chlamydia trachomatis. The probe had a nucleotide sequence of SEQ ID NO:9, designed to be complementary to one subunit of the rRNA. Unlabeled helper oligonucleotides were used to facilitate binding of the probe to the rRNA target; helper probes are described in Hogan et al., U.S. Pat. No. 5,030,557, incorporated herein by reference. Helper probes can be an aid to nucleic acid probe hybridization in certain cases (e.g., when the target analyte has considerable secondary structure) but are not, in and of themselves, part of the invention of this application. The probes used in this example were labeled with standard AE as described above.

Hybridization was conducted as follows: 3 μl (0.05 pmoles) of probe was added to 6 μl of water. This was combined with 4 μl (0.25 pmoles) of target rRNA, 2 μl (10 pmoles) of unlabeled helper probes and 15 μl of 200 mM lithium succinate (pH 5.1) and incubated at 60° C. for 40 minutes. Micelle formation and detection was performed as described in Example 2.

Figure 14:
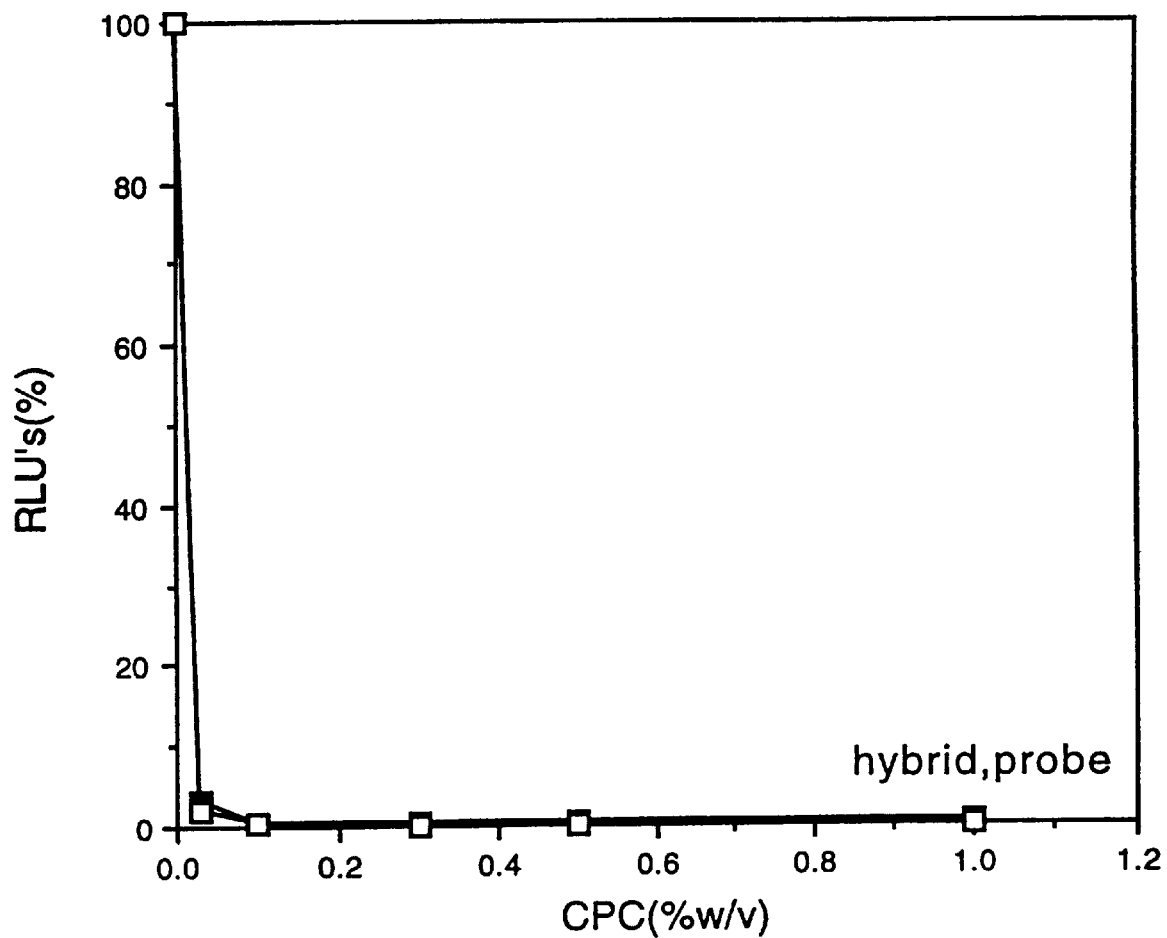
FIG. 14 is a plot of the chemiluminescence of probe-linked or hybrid-linked standard AE as a function of CPC concentration. The analyte was ribosomal RNA.

Two sets of conditions were employed for this example. In the first set, AE-labeled probe and AE-labeled hybrid were tested in the presence of increasing concentrations of CPC (0%, 0.03%, 0.1%, 0.3%, 0.5%, and 1% (w/v)). The results given below and in FIG. 14. As can be seen, the results are similar to that seen for DNA:DNA hybridization (compare with FIG. 6); addition of CPC micelles to the assay mixture results in quenching of the AE label of both probe and hybrid.

| Tube Number | Concentration CPC % (w/v) | RLU (labeled hybrid) (percent)* | RLU (labeled probe) (percent)* |
|---|---|---|---|
| 1 | 0.000 | 100.000 | 100.000 |
| 2 | 0.030 | 3.100 | 2.000 |
| 3 | 0.100 | 0.560 | 0.560 |
| 4 | 0.300 | 0.400 | 0.120 |
| 5 | 0.500 | 0.450 | 0.100 |
| 6 | 1.000 | 0.330 | 0.000 |

*100% RLU is assigned to the chemiluminescence obtained from each of the labeled probe and labeled hybrid conditions in the absence of CPC. 100% (labeled hybrid) = 56,716 RLU and 100% (labeled probe) = 35,384 RLU.

Figure 15:
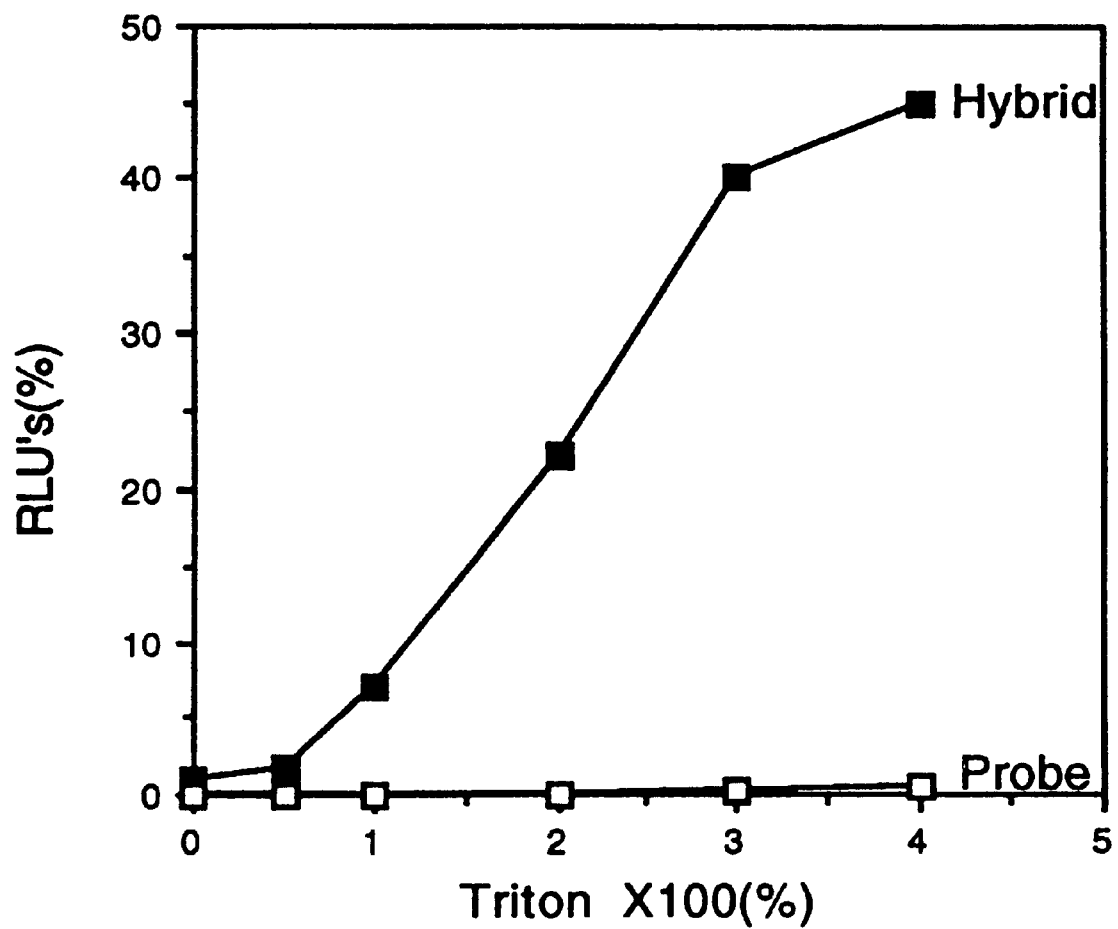
FIG. 15 is a plot of the chemiluminescence of probe-linked or hybrid-linked standard AE, in the presence of a fixed concentration of CPC, as a function of TRITON X-100 concentration. The analyte was ribosomal RNA.

FIG. 15 shows the results of adding increasing amounts of TRITON® X-100, to the labeled probe or hybrid in 0.4% (w/v) CPC. As can be clearly seen, addition of second detergent having a different hydrophobic "tail" to the reaction mixture prior to micelle formation and detection results in a strong increase in the ability of the system to distinguish free probe and labeled DNA:RNA hybrid. While not certain of the mechanism of action, Applicants believe that this increase is the result of "tuning" of the hydrophobicity of the micelle interior. The chemiluminescence of the labeled probe alone remains strongly quenched even at concentrations up to 4% (v/v) of TRITON® X-100, whereas the detectability of the labeled hybrid is greatly increased in the presence of mixed CPC:TRITON® X-100 micelles where the concentration of TRITON® X-100 is at least 4% (v/v) These results are very similar to those seen using DNA:DNA hybrids (compare FIG. 7).

| Tube Number | Concentration TRITON X-100 % (v/v) | RLU (labeled hybrid) (percent)* | RLU (labeled probe) (percent)* |
|---|---|---|---|
| 1 | 0.000 | 1.000 | 0.030 |
| 2 | 0.500 | 1.600 | 0.080 |
| 3 | 1.000 | 7.000 | 0.080 |
| 4 | 2.000 | 22.000 | 0.110 |
| 5 | 3.000 | 40.000 | 0.160 |
| 6 | 4.000 | 45.000 | 0.390 |

*100% RLU is assigned to the chemiluminescence obtained from each of the labeled probe and labeled hybrid conditions in the absence of micelles. 100% (labeled hybrid) = 56,716 RLU and 100% (labeled probe) = 35,384 RLU.

Thus, these data support the general applicability of the present method and compositions for detecting and measuring DNA and RNA analytes equally effectively. Moreover, the size of the nucleic acid target appears not to be a significant factor influencing the operation of the present invention, since the RNA analyte molecule used in the present example was considerably larger than the DNA analytes of the prior examples.

wise they are identical to standard AE. The structures of these and other AE derivatives expected to perform similarly are shown in FIG. 1; while the foregoing nomenclature for these derivatives shall be used throughout this specification, it will be clear to one of skill in the art upon examination of FIG. 1 what the precise structure of each derivative is. As mentioned above, it will be clear to one of skill in the art that these AE derivatives do not represent an exhaustive list of labels which would be expected to function in the methods and compositions of the present invention. Each AE derivative was coupled to the probe in the same manner described above. In this example the probe and DNA target analyte were of nucleotide sequence SEQ ID NOs: 1 and 2, respectively.

Hybridization was performed as follows. To a final volume of 30 μl of 0.1 M lithium succinate (pH 5.1) and 0.5 M LiCl was added 1.7 μl of probe (0.1 pmole). In the case of the tubes containing labeled hybrid, 4 μl (1 pmole) of the target oligonucleotide was also added. The tubes were incubated at 60° C. for 60 minutes.

After incubation, 10 μl of each tube's contents (each tube containing between 20,000 and 200,000 RLU of label) were added to 200 μl of detergent solution of the concentrations indicated below. The tubes were vortexed for 10 seconds, then allowed to sit at room temperature for 10 minutes. Detection was as described in Example 1.

Figure 16:
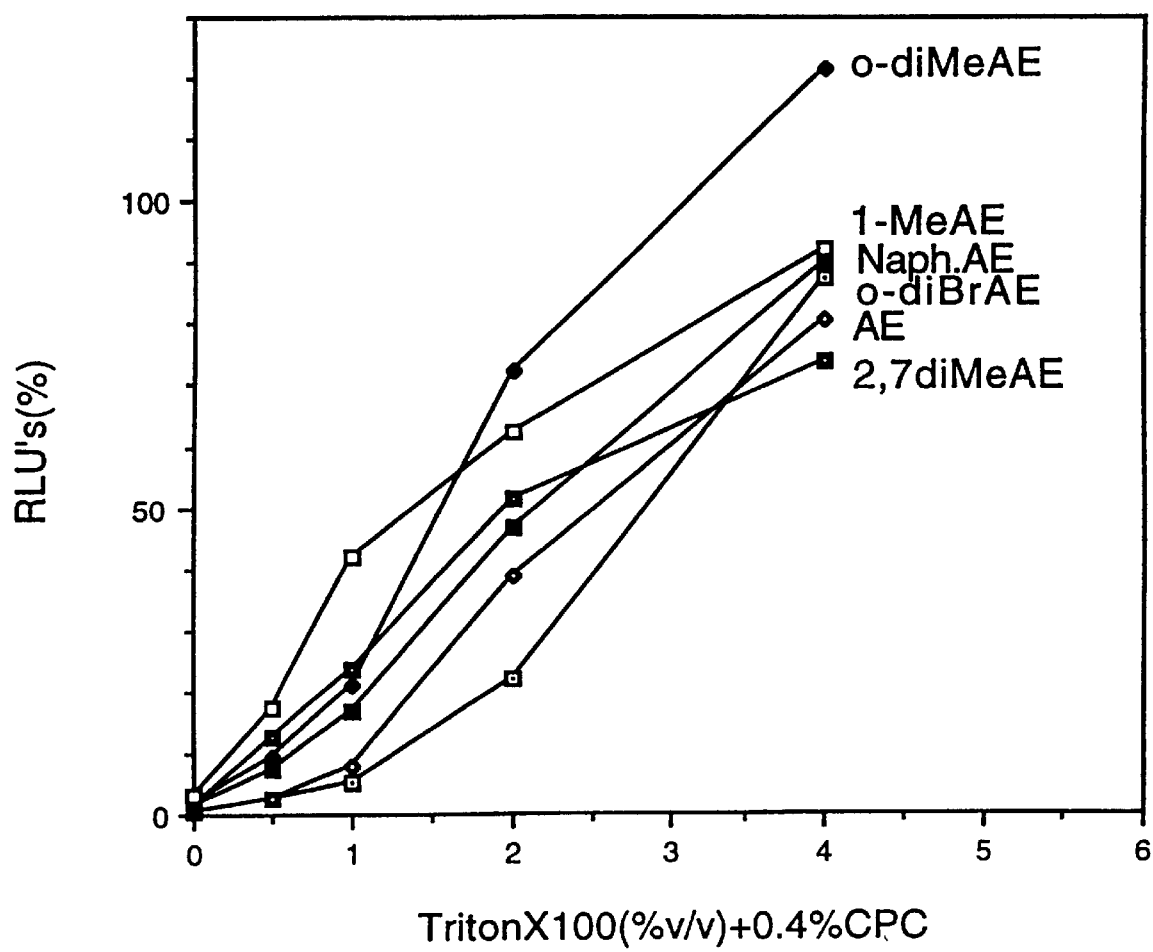
FIG. 16 is a plot of the chemiluminescence of hybrid-linked AE derivatives, in the presence of a fixed concentration of CPC, as a function of TRITON X-100 concentration.

As summarized below and in FIG. 16, the chemiluminescence of labeled hybrid containing any of the AE derivatives, including standard AE, increased similarly with increasing concentrations of non-ionic surfactant.

| Tube Number | Concentration of TRITON ® X-100 % (v/v) | o-diBr AE | | o-diMe AE | | 2,7-diMe AE | |
|---|---|---|---|---|---|---|---|
| | | RLU (labeled hybrid (percent)* | RLU (labeled probe (percent)* | RLU (labeled hybrid (percent)* | RLU (labeled probe (percent)* | RLU (labeled hybrid (percent)* | RLU (labeled probe (percent)* |
| 1 | 0.000 | 0.586 | 0.345 | 2.207 | 1.586 | 1.534 | 0.019 |
| 2 | 0.500 | 2.534 | 0.153 | 9.638 | 0.397 | 12.552 | 0.638 |
| 3 | 1.000 | 5.172 | 0.110 | 20.741 | 1.017 | 23.500 | 5.724 |
| 4 | 2.000 | 22.155 | 0.253 | 72.379 | 2.224 | 51.569 | 31.103 |
| 5 | 4.000 | 87.414 | 5.172 | 121.552 | 23.103 | 73.672 | 62.569 |
| | | Standard AE | | Naphthyl AE | | 1-Methyl AE | |
| 6 | 0.000 | 0.431 | 0.048 | 1.759 | 1.569 | 3.155 | 0.053 |
| 7 | 0.500 | 2.672 | 0.021 | 7.552 | 1.793 | 17.293 | 0.397 |
| 6 | 1.000 | 8.052 | 0.062 | 16.759 | 2.017 | 41.759 | 5.397 |
| 9 | 2.000 | 38.672 | 0.603 | 46.638 | 2.483 | 62.276 | 36.466 |
| 10 | 4.000 | 80.845 | 5.086 | 90.052 | 13.207 | 92.500 | 80.603 |

*100% RLU is assigned to the chemiluminscence obtained from each of the labeled probe and labeled hybrid conditions in the absence of micelles. 100% (standard AE-labeled hybrid) = 195,434 RLU and 100% (standard AE-labeled probe) = 108,408 RLU, 100% (0-diBr AE-labeled hybrid) = 167,288 RLU, 100% (o-diBr AE- labeled probe) = 85,761 RLU, 100% (o-diMe AE- labeled probe) = 22,401 RLU 100% (o-diMe AE- labeled probe) = 7,281 RLU, 100% (2,7-diMe AE-labeled hybrid) = 204,263 RLU, 100% (2,7-diMe AE labeled probe) = 189,596 RLU, 100% (Naphthyl AE-labeled hybrid) = 170,933 RLU, 100% (Naphthyl AE-labeled hybrid) = 25,897 RLU, 100% (1-Me AE-labeled hybrid) = 177,881 RLU, 100% (1-Me AE-labeled probe) = 146,316 RLU.

Example 14

Figure 17:
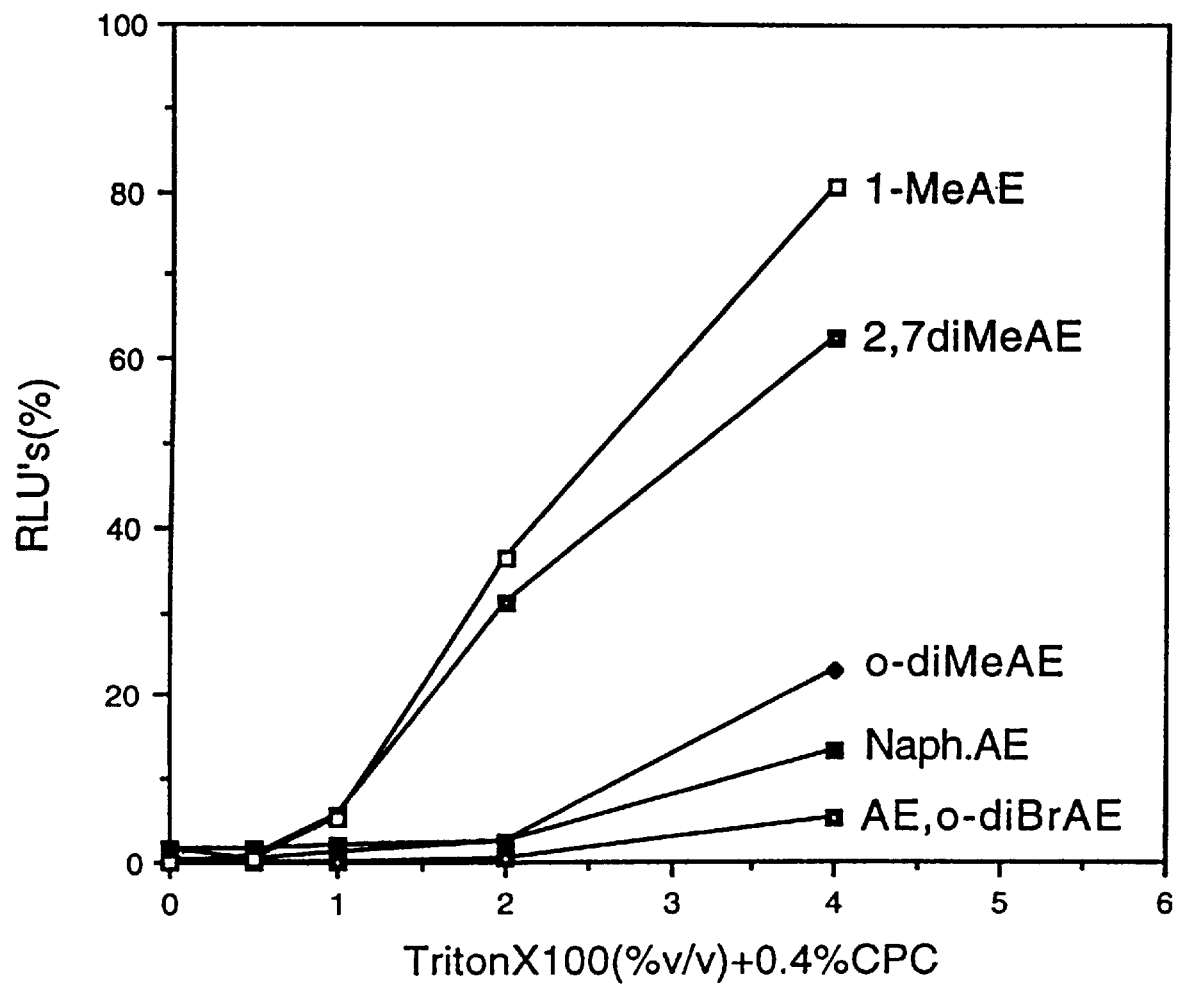
FIG. 17 is a plot of the chemiluminescence of probe-linked AE derivatives, in the presence of a fixed concentration of CPC, as a function of TRITON X-100 concentration.

In this example, different acridinium ester derivatives were coupled to the same probe and hybridized to the same target in the presence of a constant concentration of CPC and increasing concentrations of TRITON X-100 (0%, 0.5%, 1%, 2% and 4% (v/v)). Some of these derivatives have substitutions in the heterocyclic acridinium ring (1-methyl-AE, 2,7-dimethyl AE), others have substitutions on the phenyl ring (o-dimethyl-AE, o-dibromo-AE) or replace the phenyl ring with another aryl group (naphthyl-AE); other- FIG. 17 demonstrates that, under the same conditions, the same AE derivatives coupled to the same probe respond differently under these conditions when the probe is unhybridized. While the standard AE- and the o-dibromo AE-labeled free probe are both strongly quenched at higher concentrations of TRITON® X-100, the o-dimethyl AE and naphthyl AE derivatives are somewhat less strongly quenched and 1-methyl AE and 2,7-dimethyl AE-labeled probes are much less strongly quenched under these conditions.

Example 15

The ability of surfactant micelles to discriminate between labeled probe and labeled probe:analyte conjugate can depend both on the surfactant used and the structure of the labeling compound. While CPC:TRITON® X-100 mixed micelles do not, under the conditions of Example 14, allow for good discrimination between probe and hybrid when the probe is labeled with 2,7-dimethyl AE, micelles formed from BTC do allow for good discrimination between these species.

Figure 18:
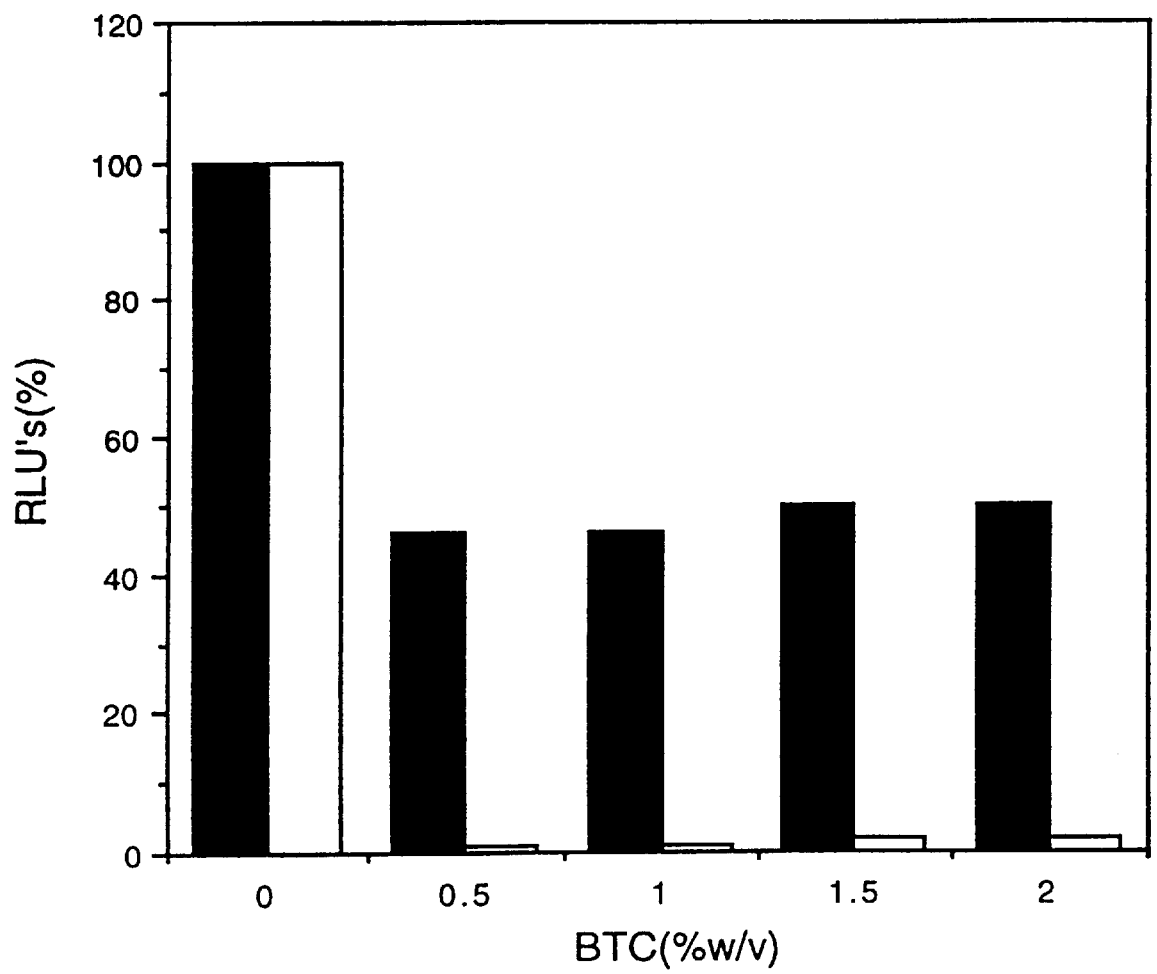
FIG. 18 is a graph showing the effect of increasing amounts of BTC on the chemiluminescence of probe-linked and hybrid-linked 2,7-diMe AE.

Assay tubes were made up containing either 2,7-dimethyl AE-labeled probe alone or the identically labeled probe:analyte hybrid. Hybridization was conducted as in Example 14. The probe and DNA target oligonucleotide were those used in Example 14. Concentrations of BTC were 0%, 0.5%, 1%, 1.5% and 2% (w/v). Micelle formation and detection was conducted as described in Example 14. Results are shown below and in FIG. 18.

| Tube Number | Concentration BTC % (w/v) | RLU (labeled hybrid) (percent)* | RLU (labeled probe) (percent)* |
|---|---|---|---|
| 1 | 0.000 | 100.000 | 100.000 |
| 2 | 0.500 | 45.900 | 1.060 |
| 3 | 1.000 | 46.200 | 1.110 |
| 4 | 1.500 | 49.800 | 1.730 |
| 5 | 2.000 | 49.900 | 1.840 |

*100% RLU is assigned to the chemiluminescence obtained from each of the labeled probe and labeled hybrid conditions in the absence of micelles. 100% (labeled hybrid) = 181,604 RLU and 100% (labeled probe) = 179,031 RLU.

As can be seen, there is no detectable discrimination between the labeled probe and labeled hybrid in the absence of micelles under these conditions. However, the addition of as little as 0.5% (w/v) BTC strongly quenches the 2,7-dimethyl AE coupled to free probe without severely quenching the chemiluminescence of the hybrid-associated label. This effects persist with increasing BTC concentrations. By contrast, BTC micelles do not discriminate well between standard AE-labeled probe and hybrid (see FIG. 8). Thus, the ability of micelles of a given composition to distinguish between labeled probe and labeled hybrid depends upon the structure of the AE derivative, in particular upon the presence and nature of substitutions of the acridinium ring.

From the present disclosure it would be a routine matter for one of ordinary skill in the art to screen micelles made of different ionic, zwitterionic and/or non-ionic surfactants, and/or surfactants with "tails" of different hydrophobicities, for their ability to discriminate between a given labeled probe and the labeled probe:analyte conjugate. Similarly, it would also be a matter of routine screening to screen different types of labels coupled to a probe molecule for the ability of the free probe and probe:analyte conjugate to be distinguished by micelles of a given fixed composition.

Example 16

This example illustrates the ability of labels other than acridinium esters derivatives to function in the method of the present invention. An NHS-derivatized rhodamine was purchased from Applied Biosystems Corp. (Foster City, Calif.) and linked to a nucleotide via a linker as detailed above. The labeled nucleotide was then incorporated into a synthetic oligonucleotide probe having the same sequence as the probe used in Example 2 above. The target DNA analyte was the same as was used in Example 2. Hybridization was conducted as follows: to 8 ml of 11 mM lithium succinate buffer (pH 5.2) was added 100 μl of probe (640 picomoles). In the tubes containing the probe:analyte hybrid, 1 ml of this solution was then added to 6.5 μl of target (2550 picomoles). Hybridization was allowed to proceed for 10 minutes at room temperature and 20 minutes at 60° C. Labeled probe or labeled hybrid were added to tubes containing either 0.4% (w/v) CTAB or 0.4% (w/v) CPC and 0%, 0.5%, 1%, 2% and 4% TRITON® X-100. Micelle formation and detection were performed as in Example 1.

| | Concentration on TRITON® X-100 % (v/v) | 0.4% (w/v) CPC | | 0.4% (w/v) CTAB | |
|---|---|---|---|---|---|
| Tube Number | | RLU (labeled hybrid) (percent)* | RLU (labeled probe) (percent)* | RLU (labeled hybrid) (percent)* | RLU (labeled probe) (percent)* |
| 1 | 0 | 0.370 | 0.280 | 0.990 | 1.020 |
| 2 | 0.500 | 0.520 | 0.460 | 1.430 | 1.720 |
| 3 | 1.000 | 0.910 | 0.720 | 1.690 | 2.380 |
| 4 | 2.000 | 2.840 | 0.950 | 3.600 | 6.000 |
| 5 | 4.000 | 23.500 | 6.650 | 11.500 | 34.800 |

Figures 19A, 19B:
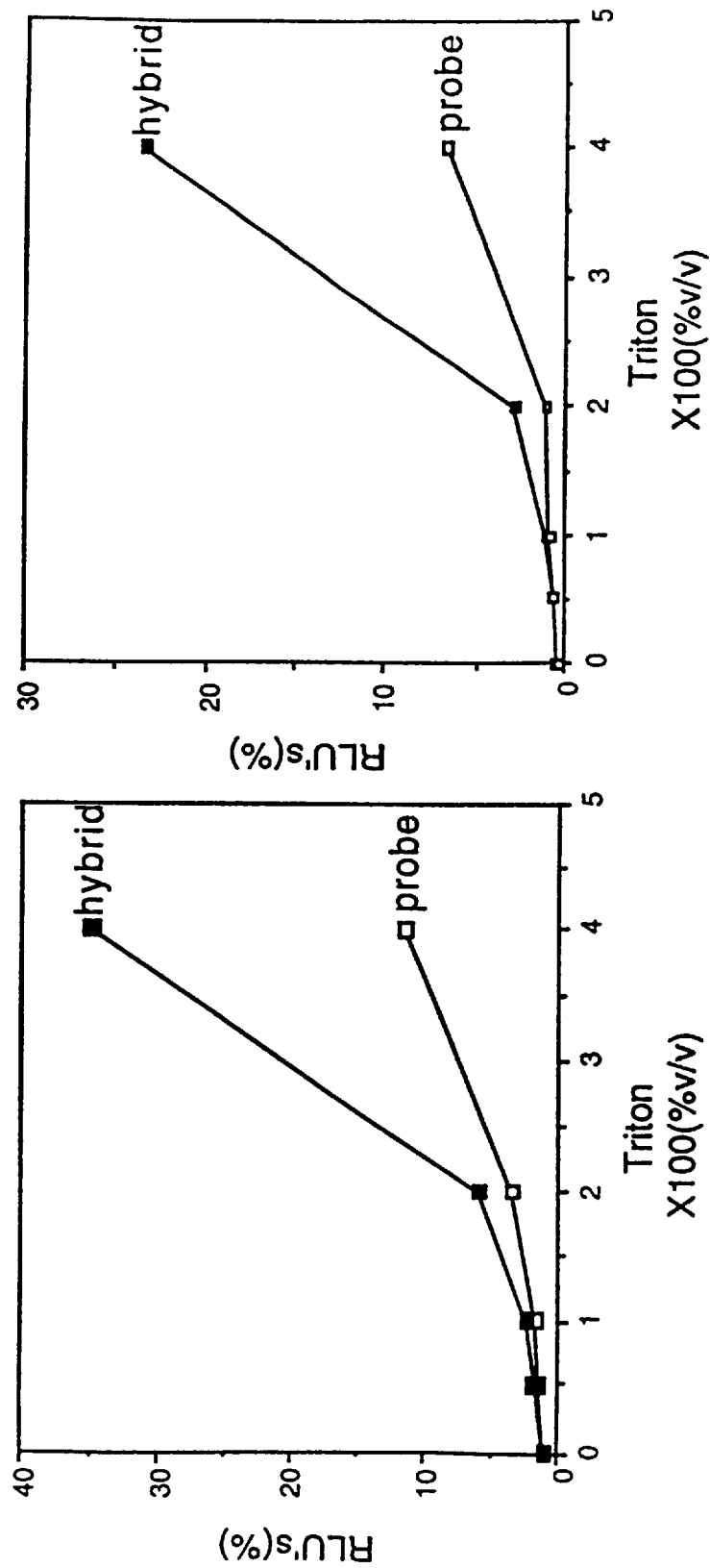
FIG. 19, heading "A" is a plot of the chemiluminescence of probe-linked and hybrid-linked rhodamine, in the presence of a fixed concentration of CTAB, as a function of increasing concentrations of TRITON X-100.

As summarized in the data and in FIG. 19, rhodamine can be used in the present invention in conjunction with micelles as a method of detecting hybrid probe:analyte complexes. The rhodamine-labeled unhybridized probe's chemiluminescent potential is strongly quenched under these conditions while the labeled hybrid remains detectable. Thus, the method of the present invention can be used with labels other than acridinium esters. Also, since the linker used to couple the rhodamine label to the probe is different than the linker used to couple AE derivatives to the probes in the previous examples, this example demonstrates that the method of linkage of label to target may be varied in the present assay without defeating the utility of this invention.

Example 17

Another aspect of the present invention is illustrated in this example. Cationic micelles are known to concentrate anions near their surface through ionic interactions. In the detection step employed in the examples of the present invention, peroxide ion (OOH—) is used to react with the chemiluminescent labels and trigger light emission. Thus, in the presence of cationic micelles, the concentration of peroxide ion required to initiate a chemiluminescent reaction would be expected to be lower than the concentration necessary to initiate a reaction having the same chemiluminescent yield in the absence of cationic micelles.

Probe and target oligonucleotides were those in Example 2; and the probe was labeled with standard AE as described above. Hybridization was conducted as described in Example 12. Micelle formation was as in Example 1. The detection step was also as described in Example 1 with the following differences: the hydrogen peroxide solution was added either at full strength, at a ten-fold dilution or at a thirty-fold dilution.

Figure 20:
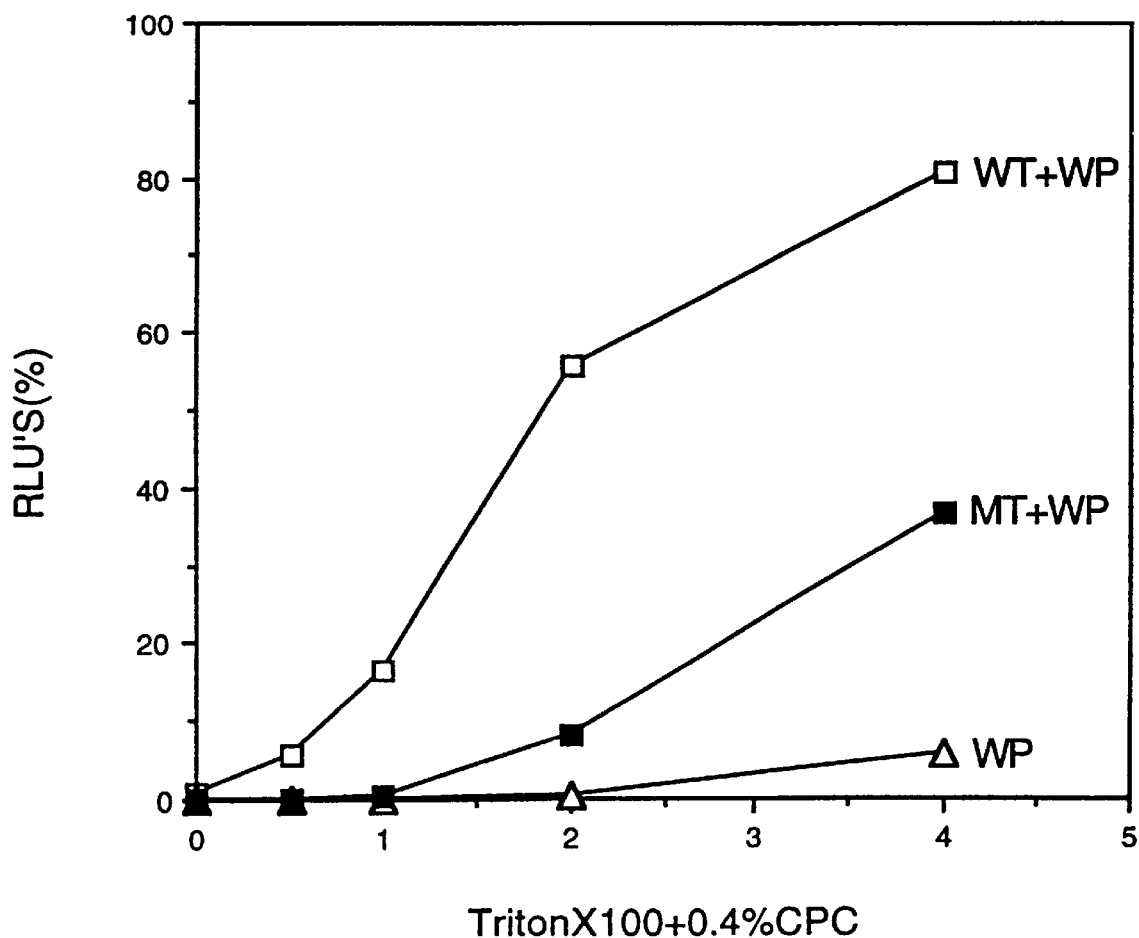
FIG. 20 is a plot of the chemiluminescence of probe-linked (WP), hybrid-linked (WT+WP), and mismatched hybrid-linked standard AE (MT+WP), in the presence of a fixed amount of CPC, as a function of TRITON X-100 concentration.

The results, illustrated below, indicate that when peroxide ion is made available at concentrations lower than under normal conditions, the chemiluminescence of unhybridized probe:analyte complex decreases in the absence of micelles. In contrast, in the presence of cationic micelles, the chemiluminescence of the probe:analyte complex drops less drastically as the concentration of of peroxide is lowered. Thus, in the presence of cationic micelles, the concentration of peroxide ion required to initiate a chemiluminescent reaction is less than the concentration required to initiate a reaction having the same chemiluminescent yield in the absence of the micelles. Additionally, the signal-to-noise ratio of the assay, determined by comparing the chemiluminescence detected from the labeled hybrid with the chemiluminescence from the free labeled probe, is improved by lowering the peroxide ion concentration.

coupled. Hybridization was performed as described in Example 14. Three sets of tubes were given 0.4% (w/v) CPC; tubes within each set were given 0%, 0.5% 1%, 2% and 4% TRITON® X-100. Micelle formation was as in Example 1. All tubes within each set were given either the perfectly matched hybrid, the mutant mismatched hybrid, or the labeled probe alone. Detection was as in Example 1. The results are shown below and in FIG. 20.

| Dilution of standard $H_2O_2$ solution (0.01% (v/v) $H_2O_2$ in 0.001 N $HNO_3$ | Micelles | Labeled Probe (RLU) | Labeled Hybrid (RLU) | Blank | % Probe | % Hybrid | % Hybrid % Probe |
|---|---|---|---|---|---|---|---|
| 1 | No | 1,824,820 | 1,851,006 | 499 | 100 | 100 | 1.0 |
| 1/10 | No | 1,075 | 833 | 117 | 0.053 | 0.039 | 0.74 |
| 1/30 | No | 217 | 129 | 115 | 0.0056 | 0.0008 | 0.14 |
| 1 | Yes | 27,158 | 756,883 | 182 | 1.48 | 40.9 | 27.6 |
| 1/10 | Yes | 5,765 | 361,820 | 442 | 0.29 | 19.5 | 67.2 |
| 1/30 | Yes | 760 | 27,341 | 124 | 0.035 | 1.47 | 42 |

Example 17

The ability of the assay of the present invention to detect mutations such as single base mismatches between a nucleic acid probe and a nucleic acid analyte is demonstrated in the present example. A probe oligonucleotide was synthesized SEQ ID NO:12 (WP). Additionally, a pair of target oligonucleotides having a single base mismatch at the same relative position (on the complementary strand) were also synthesized (SEQ ID NOs:10 (WT) and 13 (MT)). The standard AE label was linked to the probe molecules as described above; in this experiment the label was placed at a location just to the 3' side of the site of nucleotide substitution, as indicated below by an asterick. The structures resulting from hybridization of these oligonucleotides are shown below.

Each combination of probe and target indicated below was made in separate tubes; a third tube contained the "wild-type" probe alone. Hybridization and micelle formation was conducted as described in Example 14. Detection was as described in Example 1.

| Tube Number | Concentration TRITON ® X-100 % (v/v) | RLU (perfectly matched (hybrid) (percent)* | RLU (labeled probe) (percent)* | RLU (mismatched hybrid) (percent)* |
|---|---|---|---|---|
| 1 | 0.000 | 0.608 | 0.000 | 0.067 |
| 2 | 0.500 | 5.833 | 0.000 | 0.132 |
| 3 | 1.000 | 16.417 | 0.000 | 0.345 |
| 4 | 2.000 | 55.467 | 0.383 | 8.207 |
| 5 | 4.000 | 80.767 | 5.585 | 36.850 |

*100% RLU is assigned to the chemiluminescence obtained from each of the labeled probe and labeled hybrid conditions in the absence of micelles. 100% (perfectly matched labeled hybrid) = 246,540 RLU and 100% (labeled probe) = 32,381 RLU, 100% (mismatched labeled hybrid) = 206,470 RLU.

As the results indicate, the chemiluminescence of the labeled unhybridized probe is strongly quenched at all concentrations of TRITON® X-100. As demonstrated by previous examples, the chemiluminescence of the perfectly matched labeled hybrid increased with increasing concen-

| | |
|---|---|
| 5'-CCAGACATAGTTATCT-ATCAATACATGGATGAT-3' | ("Wild-type" target) -SEQ ID NO: 10 |
| 3'-GGTCTGTATCAATAGA*TAGTTATGTACCTACTA-5' | ("Wild-type" probe) - SEQ ID NO: 12; written in the 3' to 5' direction. |
| 5'-CCAGACATAGTTATCT-GTCAATACATGGATGAT-3' | ("Mismatched" target) - SEQ ID NO: 13 |
| 3'-GGTCTGTATCAATAGA*TAGTTATGTACCTACTA-5' | ("Wild-type" probe) - SEQ ID NO: 12; written in the 3' to 5' direction. |

A standard AE-coupled probe was hybridized to either a target oligonucleotide having an exactly complementary nucleotide sequence or a nucleotide sequence having a single base mismatch, with respect to the probe, at a site corresponding to the probe location at which the AE label is trations of TRITON® X-100 to about 80% of the chemiluminescent yield of the hybrid in the absence of detergent micelles.

Surprisingly, the emmission of chemiluminescent light from the labeled hybrid containing a single mismatch in the area of label attachment to the probe was also increased as the concentration of TRITON® X-100 increased, but to a lesser extent than that of the perfectly matched hybrid. It will be immediately apparent to those of skill in the art that by varying the nature and concentrations of the amphiphiles, this assay would be expected to sensitively distinguish between perfectly matched hybrids and single base mismatched hybrids as well as free probe.

Example 18

To examine whether amphiphilic molceules other than detergents can be used in the compositions and methods of the present invention, standard AE-labeled probe and unlabeled target oligonucleotides (SEQ ID NO:7 and SEQ ID NO:8) were hybridized as in Example 2. One hundred microliters of the indicated amount of a lipid preparation consisting of a 1:2.5 molar ratio of the S cationic lipid dimethyl dioctadecylammonium bromide (DDAB) to dioleoyl phosphatidyl ethanolamine (DOPE) (LipofectACE®, Gibco/BRL, Gaitersburg, Md.) was added to 2 μl of either the labeled probe alone or the labled probe:analyte complex. The resulting solution was vortexed gently and allowed to sit for 10 minutes at room temperature to form liposomes. Detection of chemiluminescence was as in Example 2. The results were as indicated below.

| % Lipofectace (w/v) | Net Probe | Net Hybrid | % Hybrid/% Probe |
|---|---|---|---|
| 0 | 598974 | 561333 | 1 |
| 0.00014 | 368846 | 474019 | 1.4 |
| 0.00028 | 217526 | 455460 | 2.3 |

-continued

| % Lipofectace (w/v) | Net Probe | Net Hybrid | % Hybrid/% Probe |
|---|---|---|---|
| 0.0014 | 145189 | 421212 | 3.1 |
| 0.0028 | 99553 | 314165 | 3.4 |
| 0.028 | 21811 | 299358 | 14.7 |
| 0.07 | 13741 | 310431 | 23.9 |

Figure 21:
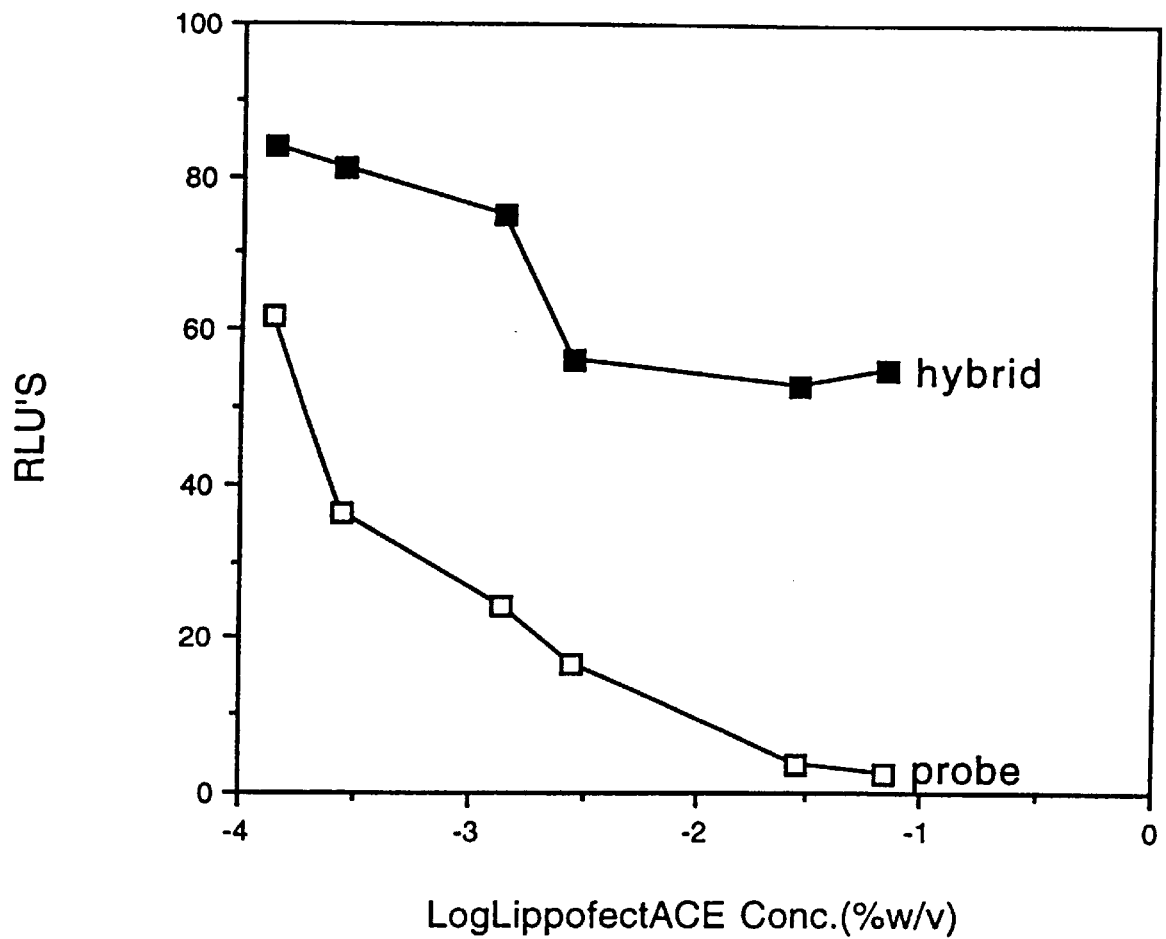
FIG. 21 is a plot of the chemiluminescence of probe-linked and hybrid-linked standard AE as a function of mixed lipid concentration.

As indicated above and in FIG. 21, the results show that the chemiluminescent potential of both labeled probe and labeled probe:analyte complex initially decreases upon the addition of low concentrations of the mixed cationic lipid preparation. At liposome concentrations of about 0.0028% (w/v) and above the chemiluminescence of the labeled probe:analyte complex remains essentially constant (at about 55% of the probe:analyte complex's chemiluminescence in the absence of liposomes), while the chemiluminescence of the labeled probe alone continues to decrease in this concentration range. Under the experimental conditions tested, discrimination between free labeled probe and labeled probe:analyte complex was greatest at 0.7% (w/v) of the LipofectASE® preparation. Thus, these data demonstrate that the present invention may be practiced with both with detergents and lipids which are less soluble in aqueous environments.

It will be understood that the foregoing examples are intended to describe particular embodiments of the present invention without limiting the invention to these embodiments. Other embodiments are contained within the following claims.

What is claimed is:

1. A method for determining the presence or amount of an analyte in a sample consisting essentially of:
 a) providing to said sample a labeled probe under conditions such that said labeled probe preferentially binds to said analyte in the presence of non-analyte, thereby forming a probe:analyte complex stable for detection;
 b) providing to said sample one or more amphiphiles which can alter the detectability of said labeled probe which does not form part of a probe:analyte complex, so that the detectability of said labeled probe which forms part of a probe:analyte complex is distinguishable from the detectability of said labeled probe which does not form part of a probe:analyte complex in the presence of said amphiphiles, wherein a charge of said probe and the charge of at least one of said amphiphiles are opposite charges; and
 c) detecting said labeled probe which forms part of a probe:analyte complex as an indication of the presence or amount of said analyte in said sample.

2. The method of claim 1 wherein the label of said labeled probe comprises a hydrophobic moiety.

3. The method of claim 1 wherein the label of said labeled probe is detected as a result of a triggering reaction between said label and a triggering agent.

4. The method of claim 1 wherein the label of said labeled probe is luminescent or fluorescent, and the luminescence or fluorescence of said label is altered when said labeled probe does not form part of a probe:analyte complex.

5. The method of claim 1 wherein the label of said labeled probe forms a detectable chemiluminescent or electrochemiluminescent species upon undergoing a triggering reaction, and the label of said labeled probe which does not form part of a probe:analyte complex is protected from the triggering agent by the presence of said amphiphiles under conditions permitting the triggering of the label of said labeled probe which forms part of a probe:analyte complex.

6. The method of claim 1 wherein at least one of said amphiphiles has a positive charge under conditions allowing the formation of a probe:analyte complex.

7. The method of claim 1 wherein at least one of said amphiphiles has a positive charge under said conditions.

8. The method of claim 1 wherein said amphiphiles include at least two different amphiphiles.

9. The method of claim 7 wherein said amphiphiles include at least two different amphiphiles.

10. The method of claim 8 wherein at least two of said amphiphiles have different hydrophobic domains.

11. The method of claim 9 wherein at least two of said amphiphiles have different hydrophobic domains.

12. The method of claim 3 wherein said label forms a detectable chemiluminescent species after undergoing said triggering reaction, said species comprising an optionally substituted, excited N-acridone.

13. The method of claim 12 wherein said label comprises an N-acridinium phenyl ester optionally substituted at the acridinium ring and at carbons 2 through 6 of the phenyl ring.

14. The method of claim 3 wherein said triggering agent is an oxidizing agent.

15. The method of claim 14 wherein said oxidizing agent is selected from the group consisting of a peroxide compound and a superoxide radical.

16. The method of claim 1 wherein said amphiphiles include a first amphiphile selected from the group consisting of the Triton® series, the Tween series, the Brij series and the NP series.

17. The method of claim 1 wherein said amphiphiles include a first amphiphile selected from the group consisting of Triton® X-100, Triton® X-305, Tween 20, Brij 35 and NP-40.

18. The method of claim 1 wherein said amphiphiles include a first amphiphile selected from the group consisting of cetyl trimethyl ammonium salts, cetylpyridinium salts, cetyl dimethylethyl ammonium salts, 3-(cyclohexylamino)-2-hydroxyl-1-propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts, benzalkonium salts, and dodecyl sulfate salts.

19. The method of claim 8 wherein said amphiphiles include a first amphiphile which is Triton® X-100 and a second amphiphile selected from the group consisting of cetyl trimethyl ammonium salts, cetylpyridinium salts, cetyl dimethylethyl ammonium salts, 3-(cyclohexylamino)-2-hydroxyl-1-propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts and benzalkonium salts.

20. The method of claim 19 wherein said second amphiphile is selected from the group consisting of cetyl trimethyl ammonium salts and cetylpyridinium salts.

21. The method of claim 13 wherein said label is selected from the group consisting of standard acridinium ester, o-dimethyl acridinium ester, 1-methyl acridinium ester, 2,7-dimethy acridinium ester, naphthyl acridinium ester, and o-dibromo acridinium ester.

22. The method of claim 1 wherein at least one of said amphiphiles is a detergent provided in an amount at least equal to the critical micelle concentration of said detergent.

23. The method of claim 1 wherein said amphiphiles are provided in an amount effective to cause the chemiluminescence of the label of said labeled probe which forms part of a probe:analyte complex to be at least four times the chemiluminescence of the label of said labeled probe which does not form part of a probe:analyte complex.

24. The method of claim 1 wherein said amphiphiles are provided in an amount effective to cause the chemiluminescence of the label of said labeled probe which forms part of a probe:analyte complex to be at least ten times the chemiluminescence of the label of said labeled probe which does not form part of a probe:analyte complex.

25. The method of claim 1 wherein said amphiphiles are provided in an amount effective to cause the chemiluminescence of the label of said labeled probe which forms part of a probe:analyte complex to be at least twenty times the chemiluminescence of the label of said labeled probe which does not form part of a probe:analyte complex.

26. The method of claim 1 wherein said amphiphiles are provided in an amount effective to cause the chemiluminescence of the label of said labeled probe which forms part of a probe:analyte complex to be at least forty times the chemiluminescence of the label of said labeled probe which does not form part of a probe:analyte complex.

27. The method of claim 1 wherein s aid amphiphiles are provided in an amount effective to cause the chemiluminescence of the label of said labeled probe which forms part of a probe:analyte complex to be at least one hundred times the chemiluminescence of the label of said labeled probe which does not form part of a probe:analyte complex.

28. The method of claim 1 wherein said amphiphiles are provided in an amount effective to cause the chemiluminescence of the label of said labeled probe which forms part of a probe:analyte complex to be at least two hundred times the chemiluminescence of the label of said labeled probe which does not form part of a probe:analyte complex.

29. A method for determining the presence or amount of a nucleic acid analyte in a sample consisting essentially of:
  a) providing to said sample a labeled nucleic acid probe under conditions such that said labeled probe preferentially binds to said analyte in the presence of non-analyte nucleic acid, thereby forming a probe:analyte complex stable for detection;
  b) providing to said sample one or more amphiphiles which can alter the detectability of said labeled probe which does not form part of a probe:analyte hybrid, so that the detectability of said labeled probe which forms part of a probe:analyte hybrid is distinguishable from the detectability of said labeled probe which does not form part of a probe:analyte hybrid in the presence of said amphiphiles, wherein a charge of said probe and the charge of at least one of said amphiphiles are opposite charges; and
  c) detecting said labeled probe which forms part of a probe:analyte hybrid as an indication of the presence or amount of said analyte in said sample.

30. The method of claim 29 wherein the label of said labeled probe comprises a hydrophobic moiety.

31. The method of claim 29 wherein the label of said labeled probe is detected as a result of a triggering reaction between said label and a triggering agent.

32. The method of claim 29 wherein the label of said labeled probe is luminescent or fluorescent, and the luminescence or fluorescence of said label is altered when said labeled probe does not form part of a probe:analyte hybrid.

33. The method of claim 29 wherein the label of said labeled probe forms a detectable chemiluminescent or electrochemiluminescent species upon undergoing a triggering reaction, and the label of said labeled probe which does not form part of a probe:analyte hybrid is protected from the triggering agent by the presence of said amphiphiles under conditions permitting the triggering of the label of said labeled probe which forms part of a probe:analyte hybrid.

34. The method of claim 29 wherein at least one of said amphiphiles has a positive charge under said conditions.

35. The method of claim 29 wherein said amphiphiles include at least two different amphiphiles.

36. The method of claim 34 wherein said amphiphiles include at least two different amphiphiles.

37. The method of claim 35 wherein at least two of said amphiphiles have different hydrophobic domains.

38. The method of claim 36 wherein at least two of said amphiphiles have different hydrophobic domains.

39. The method of claim 31 wherein said label forms a detectable chemiluminescent species after undergoing said triggering reaction, said species comprising an optionally substituted, excited N-acridone.

40. The method of claim 39 wherein said label comprises an N-acridinium phenyl ester optionally substituted at the acridinium ring and at carbons 2 through 6 of the phenyl ring.

41. The method of claim 31 wherein said triggering agent is an oxidizing agent.

42. The method of claim 41 wherein said oxidizing agent is selected from the group consisting of a peroxide compound and a superoxide radical.

43. The method of claim 29 wherein said amphiphiles include a first amphiphile selected from the group consisting of the Triton® series, the Tween series, the Brij series and the NP series.

44. The method of claim 29 wherein said amphiphiles include a first amphiphile selected from the group consisting of Triton® X-100, Triton® X-305, Tween 20, Brij 35 and NP-40.

45. The method of claim 29 wherein said amphiphiles include a first amphiphile selected from the group consisting of cetyl trimethyl ammonium salts, cetylpyridinium salts, cetyl dimethylethyl ammonium salts, 3-(cyclohexylamino)-2-hydroxyl-1-propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts, benzalkonium salts, and dodecyl sulfate salts.

46. The method of claim 35 wherein said amphiphiles include a first amphiphile which is Triton® X-100 and a second amphiphile selected from the group consisting of cetyl trimethyl ammonium salts, cetylpyridinium salts, cetyl dimethylethyl ammonium salts, 3-(cyclohexylamino)-2-hydroxyl-1-propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts and benzalkonium salts.

47. The method of claim 46 wherein said second amphiphile is selected from the group consisting of cetyl trimethyl ammonium salts and cetylpyridinium salts.

48. The method of claim 40 wherein said label is selected from the group consisting of standard acridinium ester, o-dimethyl acridinium ester, 1-methyl acridinium ester, 2,7-dimethy acridinium ester, naphthyl acridinium ester, and o-dibromo acridinium ester.

49. The method of claim 29 wherein at least one of said amphiphiles is a detergent provided in an amount at least equal to the critical micelle concentration of said detergent.

50. The method of claim 29 wherein said amphiphiles are provided in an amount effective to cause the chemiluminescence of the label of said labeled probe which forms part of a probe:analyte hybrid to be at least four times the chemiluminescence of the label of said labeled probe which does not form part of a probe:analyte hybrid.

51. The method of claim 29 wherein said amphiphiles are provided in an amount effective to cause the chemiluminescence of the label of said labeled probe which forms part of a probe:analyte hybrid to be at least ten times the chemiluminescence of the label of said labeled probe which does not form part of a probe:analyte hybrid.

52. The method of claim 29 wherein said amphiphiles are provided in an amount effective to cause the chemiluminescence of the label of said labeled probe which forms part of a probe:analyte hybrid to be at least twenty times the chemiluminescence of the label of said labeled probe which does not form part of a probe:analyte hybrid.

53. The method of claim 29 wherein said amphiphiles are provided in an amount effective to cause the chemiluminescence of the label of said labeled probe which forms part of a probe:analyte hybrid to be at least forty times the chemiluminescence of the label of said labeled probe which does not form part of a probe:analyte hybrid.

54. The method of claim 29 wherein said amphiphiles are provided in an amount effective to cause the chemiluminescence of the label of said labeled probe which forms part of a probe:analyte hybrid to be at least one hundred times the chemiluminescence of the label of said labeled probe which does not form part of a probe:analyte hybrid.

55. The method of claim 29 wherein said amphiphiles are provided in an amount effective to cause the chemiluminescence of the label of said labeled probe which forms part of a probe:analyte hybrid to be at least two hundred times the chemiluminescence of the label of said labeled probe which does not form part of a probe:analyte hybrid.

56. A composition for determining the presence or amount of an analyte in a sample comprising:
   a) a labeled probe which can be provided to a sample under conditions such that said labeled probe preferentially binds to said analyte in the presence of non-analyte, thereby forming a probe:analyte complex stable for detection; and
   b) one or more amphiphiles which can alter the detectability of said labeled probe which does not form part of a probe:analyte complex, so that the detectability of said labeled probe which does form part of a probe:analyte complex is distinguishable from the detectability of said labeled probe which does not form part of a probe:analyte complex, wherein a charge of said probe and the charge of at least one of said amphiphiles are opposite charges.

57. The composition of claim 56 wherein the label of said labeled probe is detected as a result of a triggering reaction between said label and a triggering agent.

58. The composition of claim 56 wherein the label of said labeled probe forms a detectable chemiluminescent or electrochemiluminescent species upon undergoing a triggering reaction and the label of said labeled probe which does not form part of a probe:analyte complex is protected from the triggering agent by the presence of said amphiphiles under conditions permitting the triggering of the label of said labeled probe which forms part of a probe:analyte complex.

59. The composition of claim 56 wherein at least one of said amphiphiles has a positive charge under conditions allowing the formation of a probe:analyte complex.

60. The composition of claim 56 wherein said amphiphiles include at least two different amphiphiles.

61. The composition of claim 59 wherein said amphiphiles include at least two different amphiphiles.

62. The composition of claim 60 wherein at least two of said amphiphiles have different hydrophobic domains.

63. The composition of claim 61 wherein at least two of said amphiphiles have different hydrophobic domains.

64. The composition of claim 56 wherein said probe said analyte and said non-analyte are each nucleic acids.

65. The composition of claim 57 wherein said label forms a detectable chemiluminescent species after undergoing said triggering reaction, said species comprising an optionally substituted, excited N-acridone.

66. The composition of claim 65 wherein said label comprises an N-acridinium phenyl ester optionally substituted at the acridinium ring and at carbons 2 through 6 of the phenyl ring.

67. The composition of claim 65 wherein said probe, said analyte and said non-analyte are each nucleic acids.

68. The composition of claim 58 wherein said triggering agent is an oxidizing agent.

69. The composition of claim 56 wherein a first amphiphile is selected from the group consisting of the Triton® series, the Tween series, the Brij series and the NP series.

70. The composition of claim 56 wherein a first amphiphile is selected from the group consisting of Triton® X-100, Triton® X-305, Tween 20, Brij 35 and NP-40.

71. The composition of claim 56 wherein a first amphiphile is selected from the group consisting of cetyl trimethyl ammonium salts, cetylpyridinium salts, cetyl dimethylethyl ammonium salts, 3-(cyclohexylamino)-2-hydroxyl-1-propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts, benzalkonium salts, and dodecyl sulfate salts.

72. The composition of claim 61 wherein a first amphiphile is Triton® X-100 and a second amphiphile is selected from the group consisting of cetyl trimethyl ammonium salts, cetylpyridinium salts, cetyl dimethylethyl ammonium salts, 3-(cyclohexylamino)-2-hydroxyl-1-propane sulfonate salts, benzthonium salts, benzyldimethyl salts, benzyldimethyl stearyl ammonium salts, benzyl trimethyl ammonium salts, benzylcetyldimethyl ammonium salts, benzyldimethyltetradecyl ammonium salts and benzalkonium salts.

73. The composition of claim 61 wherein a first amphiphile is Triton® X-100 and a second amphiphile is selected from the group consisting of cetyl trimethyl ammonium salts and cetylpyridinium salts.

74. The composition of claim 66 wherein said label is selected from the group consisting of standard acridinium ester, o-diMe acridinium ester, 1-Me acridinium ester, 2,7-diMe acridinium ester, naphthyl acridinium ester, and o-dibromo acridinium ester.

75. The composition of claim 72 wherein said label is selected from the group consisting of standard acridinium ester, o-diMe acridinium ester, 1-Me acridinium ester, 2,7-diMe acridinium ester, naphthyl acridinium ester, and o-dibromo acridinium ester.

* * * * *